US011007061B2

(12) United States Patent
Passman et al.

(10) Patent No.: US 11,007,061 B2
(45) Date of Patent: May 18, 2021

(54) ADJUSTABLE PERCUTANEOUS HEART VALVE REPAIR SYSTEM

(71) Applicant: Edwards Lifesciences Corporation, Irvine, CA (US)

(72) Inventors: Joseph Arthur Passman, Costa Mesa, CA (US); Omar Fawzi Azanki, Rancho Santa Margarita, CA (US); Kokou Anani Amefia, Aliso Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 16/412,224

(22) Filed: May 14, 2019

(65) Prior Publication Data

US 2019/0358029 A1 Nov. 28, 2019

Related U.S. Application Data

(60) Provisional application No. 62/675,914, filed on May 24, 2018.

(51) Int. Cl.
*A61F 2/24* (2006.01)

(52) U.S. Cl.
CPC ............ *A61F 2/246* (2013.01); *A61F 2/2466* (2013.01)

(58) Field of Classification Search
CPC .... A61F 2/246; A61F 2/89; A61F 2/90; A61F 2/91; A61F 2/915; A61F 2/958;
(Continued)

(56) References Cited

U.S. PATENT DOCUMENTS

| | | | |
|---|---|---|---|
| 5,108,413 | A | 4/1992 | Moyers |
| 5,167,239 | A | 12/1992 | Cohen et al. |

(Continued)

FOREIGN PATENT DOCUMENTS

| | | | |
|---|---|---|---|
| WO | 2006127509 | A2 | 11/2006 |
| WO | 2007050256 | A2 | 5/2007 |
| WO | 2019135907 | A1 | 7/2019 |

OTHER PUBLICATIONS

Alderson, et al., "Elastic constants of 3-, 4- and 6-connected chiral and anti-chiral honeycombs subject to uniaxial in-plane loading," Composites Science and Technology 70 (2010) 1042-1048.

(Continued)

*Primary Examiner* — Katherine H Schwiker
(74) *Attorney, Agent, or Firm* — Guy L. Cumberbatch

(57) ABSTRACT

Devices and methods for treating patients with functional tricuspid regurgitation (TR) who are unsuitable for surgery include an interoperative, adjustable-size coapting element on a catheter which may be implanted within the left or right side of the heart and extends upward into the vasculature and out of the body. The radial diameter of the coapting element can be modulated in tandem with electrocardiographic imaging to reduce valve regurgitation. One system has an elongated catheter and an expandable coapting element mounted to a distal end with an auxetic structure connected to opposite end caps. A tensioning mechanism controlled from a proximal end of the catheter is configured to pull apart the two end caps and thus elongate and radially expand the auxetic structure. Other forms of the coapting element are disclosed, as well as a kink-resistant catheter sheath having a triangular cross-section.

23 Claims, 13 Drawing Sheets

(58) Field of Classification Search

CPC .................... A61F 2/243; A61F 2/2433; A61F 2/2427–2439; A61F 2/2442–2457; A61F 2/2463; A61F 2/2466; A61F 2002/91508; A61F 2002/91516; A61F 2002/91525; A61F 2002/91533; A61F 2002/91541; A61F 2002/9155; A61F 2002/91558; A61F 2002/91566; A61F 2002/91575; A61F 2002/91583; A61F 2002/91591; A61F 2002/9583; A61F 2002/9586; A61M 25/104; A61M 2025/1084; A61M 2025/1075; A61M 2025/1061

See application file for complete search history.

(56) References Cited

U.S. PATENT DOCUMENTS 5,735,842 A 4/1998 Krueger et al.
6,009,814 A 1/2000 Rossi
6,050,972 A 4/2000 Zadno-Azizi et al.
6,217,567 B1 4/2001 Zadno-Azizi et al.
6,482,228 B1 11/2002 Norred
6,629,534 B1 10/2003 St. Goar et al.
6,702,834 B1 * 3/2004 Boylan .................. A61F 2/013 604/106
6,764,510 B2 7/2004 Vidlund et al.
6,878,320 B1 4/2005 Alderson et al.
6,994,092 B2 2/2006 van der Burg et al.
7,070,616 B2 7/2006 Majercak et al.
7,077,862 B2 7/2006 Vidlund et al.
7,160,322 B2 1/2007 Gabbay
7,320,665 B2 1/2008 Vijay
7,322,957 B2 1/2008 Kletschka et al.
7,404,824 B1 7/2008 Webler et al.
7,455,567 B2 11/2008 Bentham et al.
7,678,145 B2 3/2010 Vidlund et al.
7,785,366 B2 8/2010 Maurer et al.
7,815,580 B2 10/2010 Viswanathan
7,854,762 B2 12/2010 Speziali et al.
7,901,454 B2 3/2011 Kapadia et al.
7,927,370 B2 4/2011 Webler et al.
7,942,928 B2 5/2011 Webler et al.
8,007,428 B2 8/2011 Vijay
8,034,103 B2 10/2011 Burriesci et al.
8,070,805 B2 12/2011 Vidlund et al.
8,092,525 B2 1/2012 Eliasen et al.
8,133,213 B2 3/2012 Lashinski
8,216,302 B2 7/2012 Wilson et al.
8,449,606 B2 5/2013 Eliasen et al.
8,460,370 B2 6/2013 Zakay
8,486,136 B2 7/2013 Maurer et al.
8,579,967 B2 11/2013 Webler et al.
8,721,588 B2 5/2014 Echarri et al.
8,728,369 B2 5/2014 Alberg et al.
8,758,430 B2 6/2014 Ferrari et al.
8,758,432 B2 6/2014 Solem
8,772,187 B2 7/2014 Ugbolue et al.
8,778,017 B2 7/2014 Eliasen et al.
8,845,717 B2 9/2014 Khairkhahan et al.
8,888,843 B2 11/2014 Khairkhahan et al.
8,888,844 B2 11/2014 Eliasen et al.
8,932,348 B2 1/2015 Solem et al.
9,161,837 B2 10/2015 Kapadia
9,232,998 B2 1/2016 Wilson et al.
9,232,999 B2 1/2016 Maurer et al.
9,259,317 B2 2/2016 Wilson et al.
9,289,297 B2 3/2016 Wilson et al.
9,474,605 B2 10/2016 Rowe et al.
9,631,171 B2 4/2017 Soman et al.
9,636,223 B2 5/2017 Khalil et al.
2003/0050694 A1 3/2003 Yang et al.
2003/0120341 A1 6/2003 Shennib et al.
2003/0187494 A1 10/2003 Loaldi
2003/0212430 A1 * 11/2003 Bose ......................... A61F 2/95 606/200
2004/0098081 A1 5/2004 Landreville et al.
2004/0111108 A1 * 6/2004 Farnan ...................... A61F 2/91 606/194
2004/0225233 A1 11/2004 Frankowski et al.
2004/0267280 A1 12/2004 Nishide et al.
2006/0129227 A1 6/2006 Hengelmolen
2006/0241745 A1 10/2006 Solem
2007/0162071 A1 7/2007 Burkett et al.
2007/0162112 A1 7/2007 Burriesci et al.
2007/0198082 A1 8/2007 Kapadia et al.
2007/0219627 A1 9/2007 Chu et al.
2007/0255399 A1 11/2007 Eliasen et al.
2007/0265700 A1 11/2007 Eliasen et al.
2007/0270943 A1 11/2007 Solem et al.
2007/0282429 A1 12/2007 Hauser et al.
2009/0048668 A1 2/2009 Wilson et al.
2009/0069885 A1 3/2009 Randert et al.
2009/0137968 A1 5/2009 Rottenberg
2009/0228093 A1 * 9/2009 Taylor .................. A61F 2/2418 623/1.12
2010/0022948 A1 1/2010 Wilson et al.
2010/0198347 A1 8/2010 Zakay et al.
2010/0298929 A1 11/2010 Thornton et al.
2011/0029063 A1 2/2011 Ma et al.
2011/0077733 A1 3/2011 Bolen
2011/0184512 A1 7/2011 Webler et al.
2011/0224784 A1 9/2011 Quinn
2011/0282452 A1 11/2011 Koerner et al.
2012/0143320 A1 6/2012 Eliasen et al.
2013/0190798 A1 * 7/2013 Kapadia ................ A61F 2/2466 606/195
2013/0238086 A1 9/2013 Ballard et al.
2013/0325110 A1 * 12/2013 Khalil .................. A61F 2/2463 623/2.11
2013/0338763 A1 * 12/2013 Rowe .................... A61F 2/2427 623/2.11
2014/0309732 A1 10/2014 Bolen
2015/0224290 A1 * 8/2015 Chanduszko ........... A61F 2/958 600/585
2017/0143478 A1 * 5/2017 Schwartz .............. A61F 2/2466
2018/0207412 A1 * 7/2018 Malek ................... A61M 25/04
2018/0243087 A1 * 8/2018 Kapadia ................ A61F 2/2466
2018/0304052 A1 * 10/2018 Schneider ......... A61M 25/1002
2019/0209306 A1 7/2019 Passman et al.

OTHER PUBLICATIONS

Gatt et al., "A realistic generic model for anti-tetrachiral systems," Phys. Status Solidi B 250, No. 10, 2012-2019 (2013).
Lakes, R.S., et al., "Foam Structures with a Negative Poisson's Ratio," Science. Feb. 27, 1987;235(4792):1038-40.
Smith, et al., "A Novel Mechanism for Generating Auxetic Behaviour in Reticulated Foams: Missing Rib Foam Model," Acta Materialia vol. 48, Issue 17, Nov. 8, 2000, pp. 4349-4356.

* cited by examiner

90

90

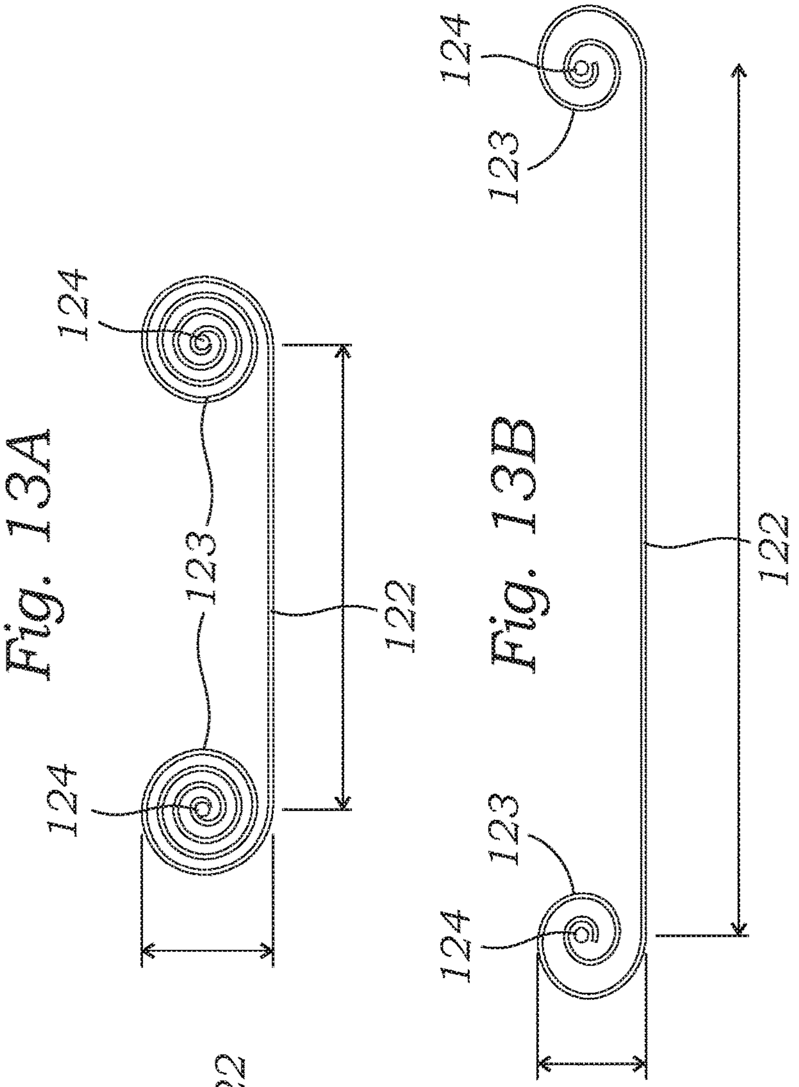
Fig. 13A
Fig. 13B
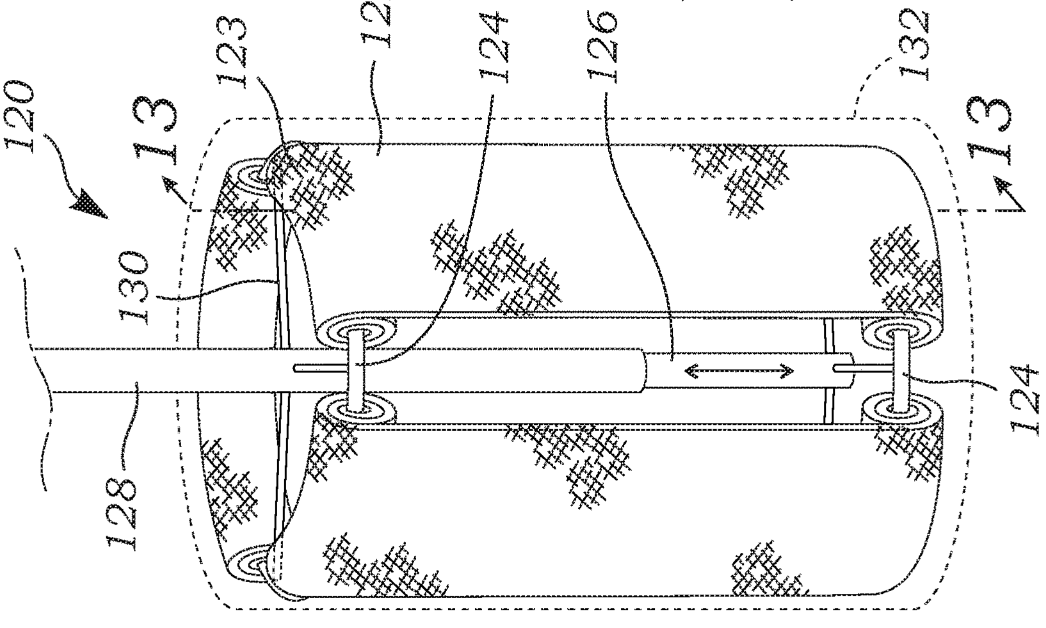
Fig. 12

ADJUSTABLE PERCUTANEOUS HEART VALVE REPAIR SYSTEM

RELATED APPLICATIONS

The present application claims priority under 35 U.S.C. § 119 to U.S. Provisional No. 62/675,914, filed May 24, 2018, the contents of which are expressly incorporated herein.

FIELD OF THE INVENTION

The present invention relates generally to devices and methods for reducing regurgitation through an atrioventricular heart valve and, more particularly, to adjustable coaptation elements positioned within the valve leaflets to reduce regurgitation.

BACKGROUND OF THE INVENTION

Heart valve disease, such as valve regurgitation, is typically treated by replacing or repairing the diseased valve during open-heart surgery. However, open-heart surgery is highly invasive and is therefore not an option for many patients. For high-risk patients, a less-invasive method for repair of heart valves is considered generally advantageous.

Functional tricuspid regurgitation (TR), which accounts for the majority of all TR cases, occurs as a result of dilatation of the tricuspid annulus and enlargement of the right ventricle. These symptoms are often secondary to pulmonary hypertension, RV dysfunction, and left-sided valvular heart disease. Although early investigators hypothesized that TR would resolve upon correction of left-sided heart disease, subsequent studies have shown that severe TR often persists after left-sided valve interventions. Additionally, functional TR is increasingly recognized as a source of morbidity and a predictor for poor long-term survival. Because the native valve leaflets typically exhibit no abnormal morphology in cases of functional TR, annular remodeling with a prosthetic ring has become the current gold standard for treatment.

One solution is seen in U.S. Pat. No. 9,474,605, which discloses a heart valve repair system for reducing regurgitation through a native valve. A flexible rail having a ventricular anchor on the distal end thereof adapted to anchor into tissue within a ventricle is first deployed percutaneously. A repair catheter passes along the flexible rail, and a leaflet coaptation member on a distal end of the catheter is positioned within the native valve leaflets. Once placed correctly, the coaptation member reduces or eliminates regurgitation through the native valve, in particular a tricuspid heart valve.

Despite existing solutions, there is still a need for a more flexible system for reducing regurgitation that can accommodate various patient's anatomies and pathologies.

SUMMARY OF THE INVENTION

The present invention relates generally to devices and methods for reducing regurgitation through an atrioventricular heart valve and, more particularly, to adjustable coaptation elements positioned within the valve leaflets to reduce regurgitation. The adjustable-size coapting element is delivered on a catheter which may be implanted within the left or right side of the heart and extends upwardly into the vasculature and out of the body. The radial diameter of the coapting element can be modulated in tandem with electrocardiographic imaging to reduce valve regurgitation. One system has an elongated catheter and an expandable coapting element mounted to a distal end with an auxetic structure that exhibits a negative Poisson's ratio, wherein the coapting element radially expands when tension is applied along a longitudinal axis. This unique structural quality has numerous benefits in the context of a coaption element for blocking valve regurgitation.

In one embodiment, an elongated percutaneously-implanted device for preventing regurgitation through a native heart valve includes an elongated catheter having a length sufficient to extend from outside the body to a native heart valve via the subclavian vein and superior vena cava. An expandable coapting element mounted to a distal end of the catheter has an auxetic structure configured to exhibit a negative Poisson's ratio connected to opposite end caps. A tensioning mechanism controlled from a proximal end of the catheter is configured to apply tension tending to pull apart the two end caps and thus elongate and radially expand the auxetic structure.

In the aforementioned system, the auxetic structure may be a metallic stent having an anti-tetrachiral strut pattern. The tensioning mechanism preferably extends through the metallic stent between the end caps and includes a plurality of flexible actuation rods that pass through the catheter sheath and through a proximal end cap. The actuation rods act on a first cam member to rotate a second cam member and advance a nut over a threaded rod, the nut causing a distal end cap to be displaced distally with respect to the proximal end cap. Alternatively, the tensioning mechanism comprises a piston-cylinder assembly that extends through the metallic stent between the end caps and is supplied with an inflation fluid through a flexible secondary catheter that passes through the catheter sheath.

In another form, the auxetic structure is an auxetic foam. The auxetic foam is preferably formed in a tube disposed in a middle portion of the coapting element. The tensioning mechanism extends through the auxetic foam tube between the end caps and may comprise a telescoped arrangement of a female end of a delivery catheter that engages a male threaded shaft secured to the distal end cap. In a preferred embodiment, the end caps comprise self-expanding stents that expand outward in the absence of any radial constraints to be larger in diameter than the auxetic foam tube.

An alternative elongated percutaneously-implanted system for preventing regurgitation through a native heart valve comprises an elongated catheter sheath having a length sufficient to extend from outside the body to a native heart valve via the subclavian vein and superior vena cava. An expandable coapting element mounts to a distal end of the catheter sheath, the coapting element having an adjustable-diameter mid-portion. An adjustment mechanism within the coapting element is controlled from a proximal end of the catheter sheath and configured to radially expand the adjustable-diameter mid-portion.

Alternatively, the adjustable-diameter mid-portion may be an auxetic structure configured to exhibit a negative Poisson's ratio connected to opposite longitudinal end caps, and the adjustment mechanism includes a tensioning mechanism configured to apply tension tending to pull apart the two end caps and thus elongate and radially expand the auxetic structure. The auxetic structure may a metallic stent having an anti-tetrachiral strut pattern, or may be an auxetic foam.

Alternatively, the expandable coapting element comprises a plurality of strips that are concentrically spaced and coiled at proximal and distal ends around proximal and distal end rings, where the distance between the end rings may be adjusted via a telescoped smaller tube within a larger tube, the tubes being respectively coupled to the end rings via spokes.

In a still further embodiment, the expandable coapting element comprises an outer cover, an inner balloon, and an intermediate stent sandwiched therebetween and the catheter sheath includes an inflation lumen for increasing or decreasing the pressure within the inner balloon.

In another alternative, the expandable coapting element comprises an outer cover including a stent connected to a rotating core via spirally-dispersed, curved cantilever spokes, wherein rotation of the rotating core straightens the curved cantilever spokes and expands the outer cover.

In another alternative, the expandable coapting element comprises a plurality of radially movable members within and in contact with an outer cover, and a camming member that radially displaces the movable members outward upon axial displacement therebetween.

Any of the aforementioned systems may include a hyper-compliant polymeric outer cover surrounding the expandable structure, and the elongated catheter sheath preferably has a kink-resistant mid-portion that has a triangular cross-sectional shape.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

To further clarify various aspects of embodiments of the present disclosure, a more particular description of the certain embodiments will be made by reference to various aspects of the appended drawings. It is appreciated that these drawings depict only typical embodiments of the present disclosure and are therefore not to be considered limiting of the scope of the disclosure. Moreover, while the figures may be drawn to scale for some embodiments, the figures are not necessarily drawn to scale for all embodiments. Embodiments of the present disclosure will be described and explained with additional specificity and detail through the use of the accompanying drawings.

FIG. 12 is a side view of an adjustable coapting element having a number of coiled strips which alter a shape of the element;

FIGS. 13A and 13B are sectional views through one of the coiled strips in FIG. 12 in coiled and uncoiled states;

DETAILED DESCRIPTION OF THE PREFERRED EMBODIMENTS

The following description refers to the accompanying drawings, which illustrate specific embodiments of the invention. Other embodiments having different structures and operation do not depart from the scope of the present invention.

Various embodiments of the present disclosure are directed to devices and methods for treating patients with functional tricuspid regurgitation (TR) who are not well-suited for surgery. Existing technology, as disclosed in U.S. Pat. No. 9,474,605, expressly incorporated herein, restores leaflet coaptation by utilizing a spacer for plugging a regurgitant hole between leaflets of a tricuspid valve.

In testing of current systems, the size of the spacer needs to be roughly equivalent to the size of the regurgitant hole in order to reduce triscuspid regurgitation (TR) completely. If the spacers are under-sized then regurgitation still occurs, while an over-sized spacer may initiate stenosis or reduce or even block blood flow from the right atrium to the right ventricle. Spacers are available in several discrete sizes (e.g., 12 mm, 15 mm, and 18 mm). Extensive imaging work is currently undertaken to ensure that the spacer is appropriately sized for the patient's anatomy. In addition or alternatively, a sizing balloon catheter may be used to measure appropriate spacer sizes preoperatively. Although the sizing balloon theoretically addresses the need for an appropriately sized spacer, this design solution adds complexity and time to the procedure. In addition, it increases the cost of the system and increases the burden on manufacturing.

The present invention advantageously provides an inter-operative, adjustable size spacer. The spacer's radial diameter can be modulated in tandem with electrocardiographic imaging to reduce the grade of valve regurgitation with minimal complexity. The application thus relates to mechanisms for modulating the diameter of an implant for the purpose of more effectively reducing cardiac valve regurgitation.

A particular application of such devices and methods disclosed herein involves an implanted heart valve regurgitation reduction system which may be implanted within the left or right side of the heart and extends upwardly into the vasculature, for example, to the subclavian vein.

Figure 1:
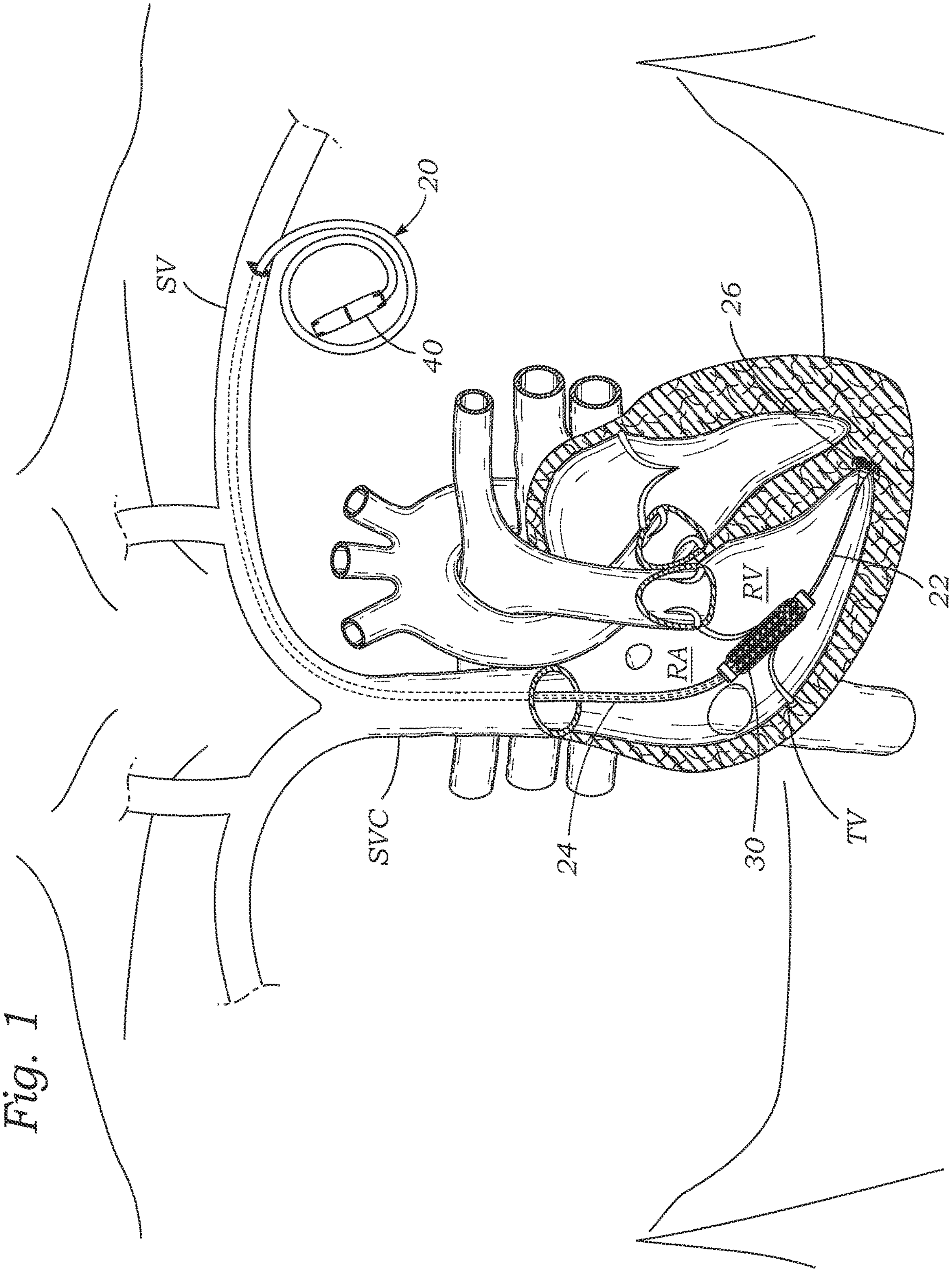
FIG. 1 is a schematic view of the final configuration of a percutaneous heart valve regurgitation reduction system having an adjustable coapting element positioned within the tricuspid valve and a proximal length of the repair catheter including a locking collet shown exiting the subclavian vein to remain implanted subcutaneously.

FIG. 1 is a schematic view of the implanted configuration of a percutaneous heart valve regurgitation reduction system having an adjustable coapting element positioned within the tricuspid valve and a proximal length of the repair catheter including a locking collet shown exiting the subclavian vein to remain implanted subcutaneously. The system includes a repair catheter 20 percutaneously delivered into the right side of the heart to reduce tricuspid valve TV regurgitation. The repair catheter 20 preferably enters the right atrium RA from the superior vena cava SVC after having been introduced to the subclavian vein SV using well-known methods, such as the Seldinger technique. The repair catheter 20 preferably tracks over a pre-installed anchor rail 22 that has also been inserted into the subclavian vein SV and steered through the vasculature until it resides and is anchored at the apex of the right ventricle RV, as shown. The repair catheter 20 includes an elongated hollow sheath 24 that may be reinforced with an embedded braided or coiled structure.

A device anchor 26 is provided for engaging tissue and thereby securing the rail 22 at or near the apex of the right ventricle RV. The anchor rail 22 may be constructed as a braided wire rod, or cable, and is desirably hollow so as to enable passage over a guide wire. Further details of the anchor rail 22 and device anchor 26 are seen in U.S. Pat. Nos. 8,932,348 and 9,474,605, both of which are expressly incorporated herein by reference.

The repair catheter sheath 24 carries an adjustable coapting element 30 on its distal end which is ultimately positioned within the tricuspid valve TV, the leaflets of which are shown closed in systole and in contact with the coapting element. A variety of adjustable coapting elements may be utilized, as disclosed herein, the common feature of which is the goal of providing an adjustable plug of sorts within the heart valve leaflets to mitigate or otherwise eliminate regurgitation. In the illustrated embodiment, the coapting element 30 includes an expandable body which may be adjusted in vivo. Other coapting elements are disclosed in U.S. Pat. Nos. 9,474,605 and 9,636,223, both of which are expressly incorporated herein by reference. The coapting element 30 is delivered in a radially contracted state to reduce the size of the incisions and enable passage through the vasculature, is then expanded within the valve leaflets, and then adjusted based on real-time data to maximize performance. Specifically, the physician has the ability for real time adjustment of the performance of the coapting element 30 under fluoroscopy or other form of visualization.

In one preferred embodiment, the coapting element 30 includes an auxetic structure that radially expands when subjected to a longitudinal tensile force. More particularly, the coapting element 30 includes a midsection having negative Poisson's ratio properties. Examples of such structures include a laser-cut, pre-compressed anti-tetrachiral pattern such as described below.

A locking mechanism is provided on the regurgitation repair catheter 20 to lock the position of the coapting element 30 within the tricuspid valve TV and relative to the fixed anchor rail 22. For example, a locking collet 40 along the length of the repair catheter sheath 24 permits the physician to selectively lock the position of the sheath 24 over the anchor rail 22, and thus the connected coapting element 30 along the rail 22. There are of course a number of ways to lock a catheter over a concentric guide rail, and the application should not be considered limited to the illustrated embodiment. For instance, rather than a locking collet 40, a crimpable section such as a stainless steel tube may be included on the repair catheter sheath 24 at a location near the skin entry point and spaced apart from the location of the coapting element 30. The physician need only position the coapting element 30 within the leaflets, crimp the catheter sheath 24 onto the anchor rail 22, and then sever both the catheter and rail above the crimp point.

A proximal length of the repair catheter 20 including the locking collet 40 exits the subclavian vein SV through a sealed puncture and preferably remains implanted subcutaneously; such as by coiling upon itself as shown. In the procedure, the physician first ensures proper positioning of the coapting element 30 within the tricuspid valve TV, locks the repair catheter 20 with respect to the anchor rail 22 by actuating the locking collet 40, and then severs that portion of the repair catheter sheath 24 that extends proximally from the locking collet. The collet 40 and/or coiled portion of the repair catheter sheath 24 may be sutured or otherwise anchored in place to subcutaneous tissues outside the subclavian vein SV. It is also worth noting that since the repair catheter 20 initially slides with respect to the anchor rail 22, it may be completely removed to withdraw the coapting element 30 and abort the procedure prior to implantation. The implant configuration is similar to that practiced when securing a pacemaker with an electrode in the right atrium muscle tissue and the leads extending to the associated pulse generator placed outside the subclavian vein. In fact, the procedure of the present invention may be performed in conjunction with the implant of a pacing lead.

Auxetic Expanders

Figure 2A:
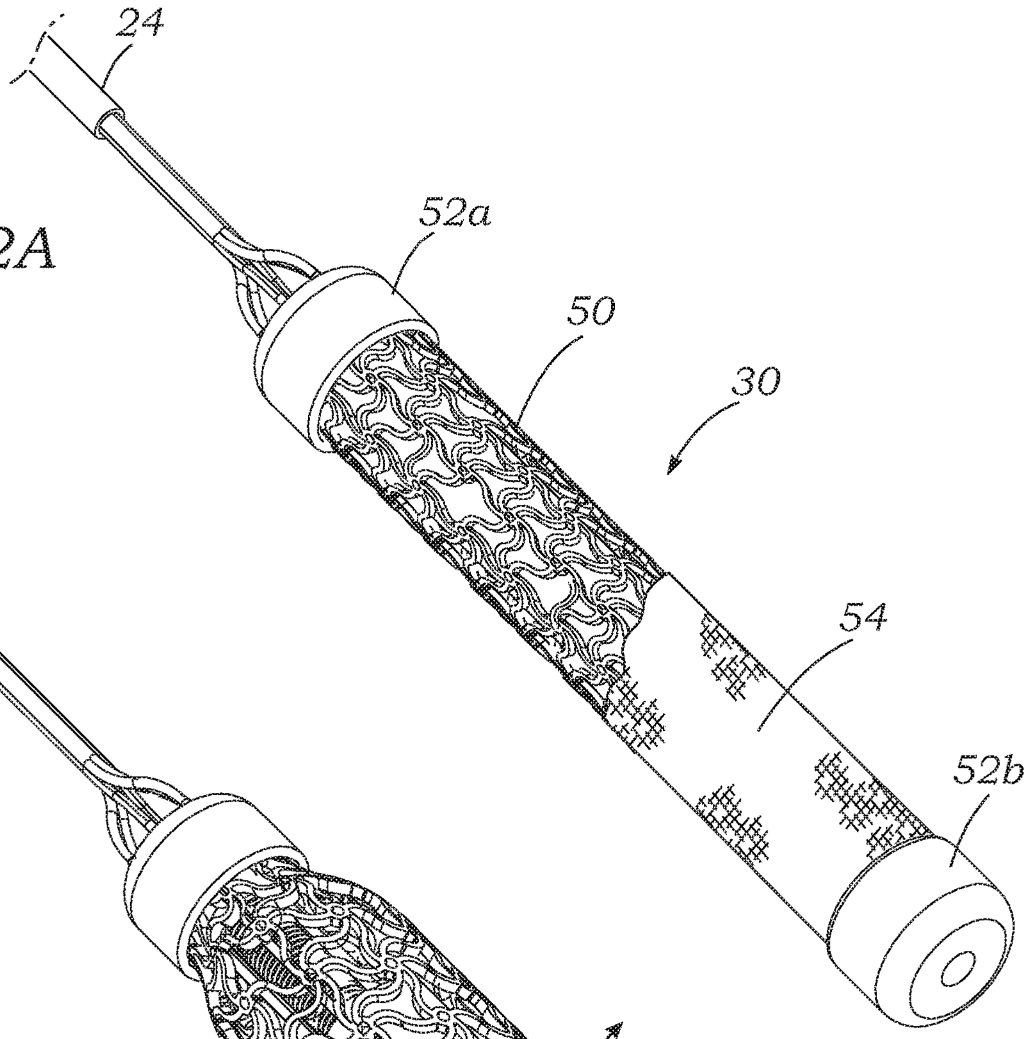
FIG. 2A is a perspective view of the adjustable coapting element with an auxetic structure in a contracted state.
Figure 2B:
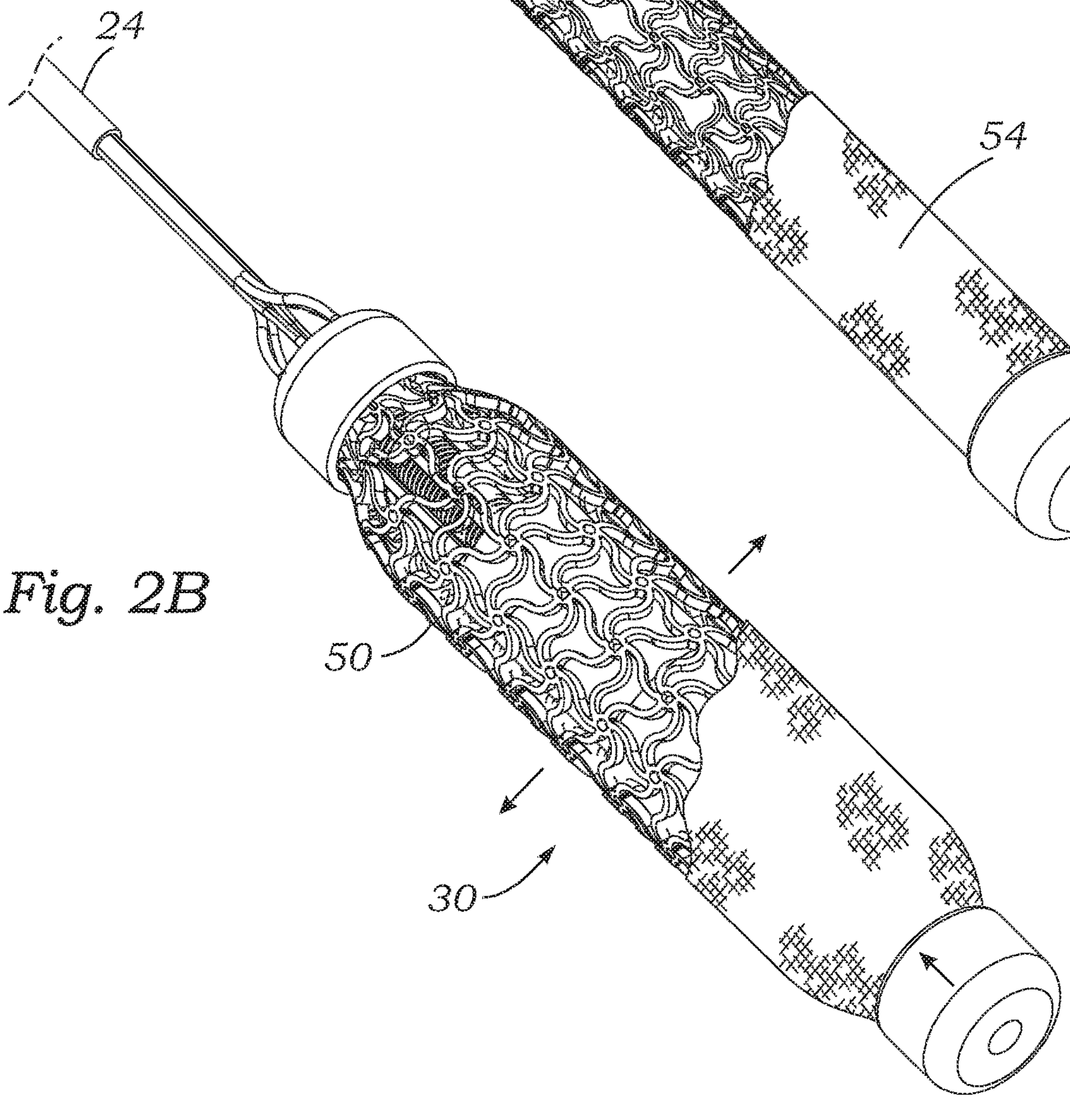
FIG. 2B shows the adjustable coapting element in an expanded state.

FIG. 2A is a perspective view of the adjustable coapting element 30 with an auxetic structure in a contracted state. FIG. 2B illustrates the adjustable coapting element 30 in an expanded state. The coapting element 30 includes an auxetic shape memory alloy stent 50 extending between a proximal end cap **52*a* and a distal end cap 52*b*. An outer cover 54 shown partly cutaway may be a suitable polymer or even bioprosthetic tissue. In a preferred embodiment, the outer cover 54** is a hyper-compliant polymeric cover made of Carbothane™. Carbothane is a family of aliphatic and aromatic, polycarbonate-based thermoplastic polyurethanes (TPUs) that are available in a wide range of hardnesses, colors, and radiopacifiers. Carbothane TPUs have desirable properties such as resistance to bodily fluids, good oxidative and biocompatible properties. It should be understood that, unless mentioned otherwise, each of the various expandable coapting elements described herein has an outer cover, which may be formed of the various options discussed herein and, in particular, a cover made of hyper-compliant polymer, preferably a polycarbonate-based thermoplastic polyurethane such as Carbothane™. The term "hyper-compliant" refers to a material that is highly compliant and elastic. An exemplary cover material is 95A Shore hardness, but a softer material may be desirable, such as any material with a Shore hardness of greater than 20A.

As will be described below, the coapting element 30 has internal components that enable a longitudinal tensile force to be exerted on the stent 50, which causes it to radially expand due to its material and auxetic structure. The outer cover 54 closely surrounds the stent 50 and expands therewith. In this way, the radial size of the coapting element 30 may be advantageously adjusted after having been positioned between the regurgitant valve leaflets, which enables the surgeon to fine-tune the performance of the element.

As noted above, an auxetic structure is a structure that exhibits a negative Poisson's ratio. Poisson's ratio expresses the relative nature of a material to contract or expand transversely under axial strain. Conventional structures or materials contract transversely when subjected to axial strain, exhibiting positive Poisson's ratio. The opposite behavior—expanding under axial loading—results in a negative Poisson's ratio. An auxetic (or negative Poisson's ratio) structure or material expands in all directions when pulled in only one, behaving in an opposite way compared with "classical" materials. Chiral shape memory alloy honeycombs have been discussed in the scientific literature for their abilities to exhibit negative Poisson's ratio. The expandable section of the stent 50 has a laser-cut, pre-compressed anti-tetrachiral pattern, and is more fully described below with respect to FIGS. 8A and 8B.

Figure 3:
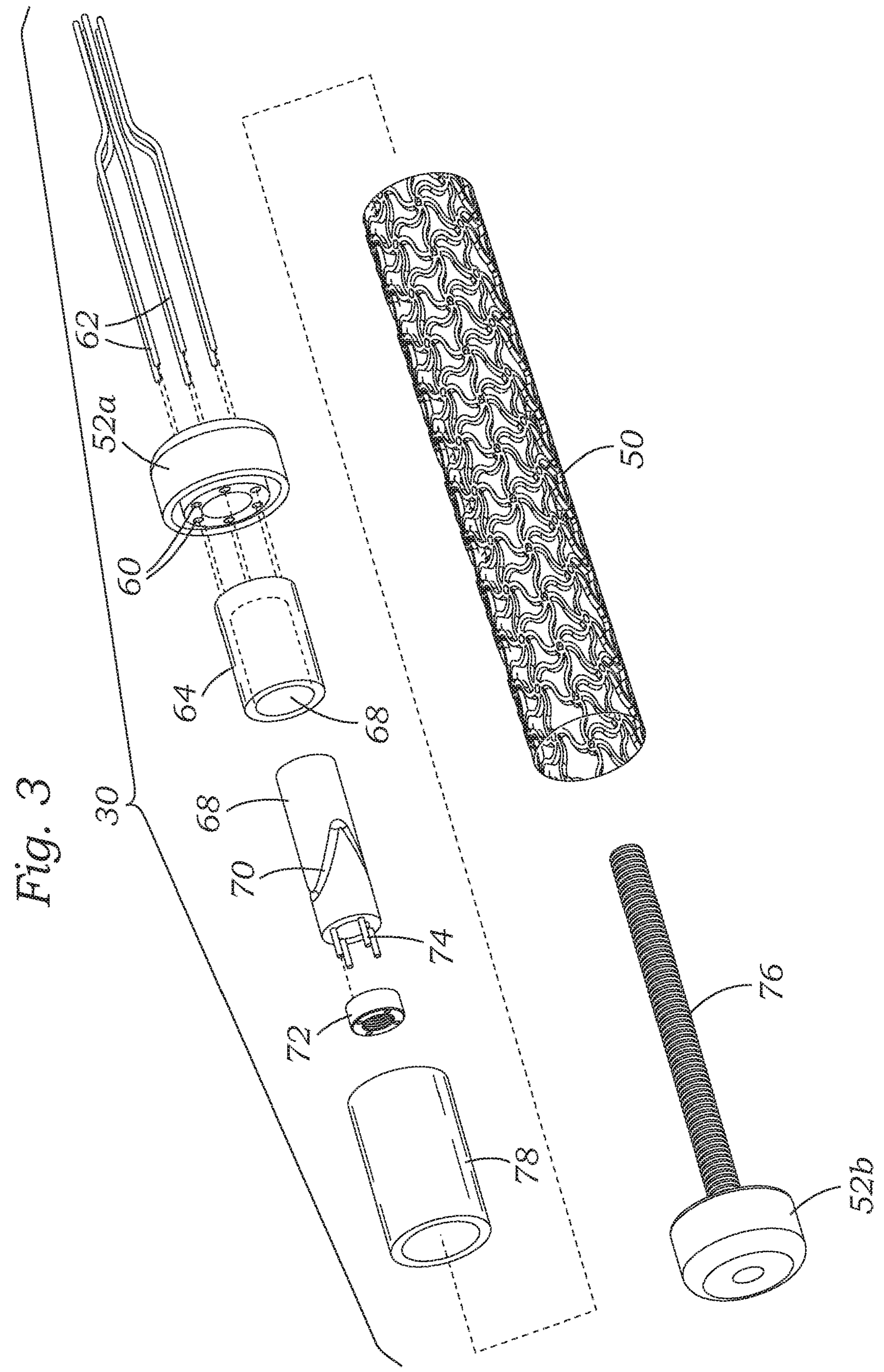
FIG. 3 is an exploded perspective view of the adjustable coapting element showing internal components.
Figures 4A, 4B:
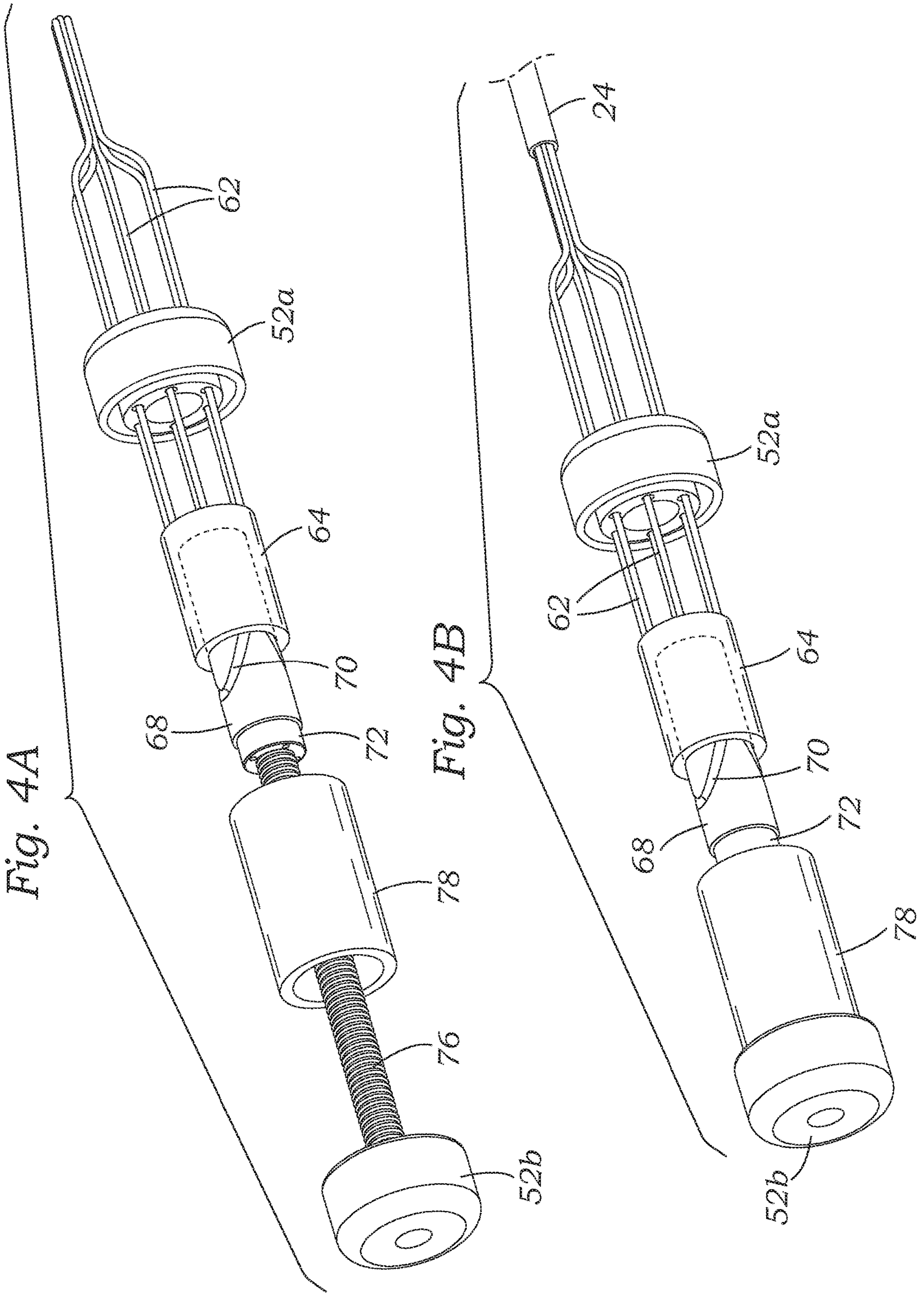
FIG. 4A is a partly assembled perspective view of the adjustable coapting element without an auxetic shape memory alloy stent.
FIG. 4B shows the fully assembled adjustable coapting element prior to actuation of an internal tensioning mechanism.
Figure 4C:
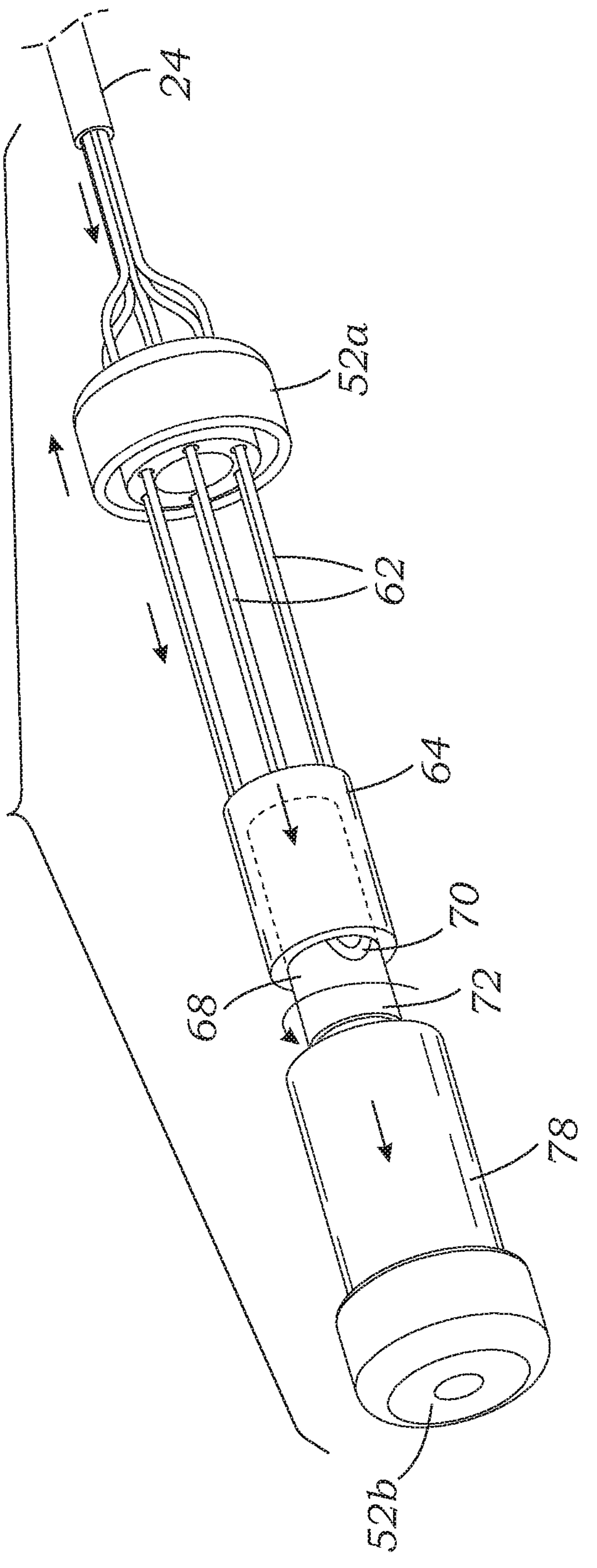
FIG. 4C shows the coapting element after actuation of the internal tensioning mechanism.

With reference now to a preferred embodiment illustrated in FIG. 3, an exploded perspective view of the adjustable coapting element 30 illustrates the proximal and distal end caps 52*a*, 52*b* along with a number of internal components that enable expansion of the stent 50. FIG. 4A is a partly assembled perspective view of the adjustable coapting element 30. FIG. 4B shows the fully assembled adjustable coapting element prior to actuation of an internal tensioning mechanism. FIG. 4C shows the coapting element after actuation of the internal tensioning mechanism.

The proximal end cap 52*a* has a plurality of axial through holes 60 that each receives an elongated and flexible actuation rod 62. Distal ends of the actuation rods 62 are secured within or to a male cam member 64 which has a tubular distal end 66 sized to slide over a generally tubular female cam member 68. The female cam member 68 defines an undulating groove 70 which may be formed as a continuous channel as shown or in separate channels. Although not shown, the male cam member 64 features a diametrically-opposite pair of inwardly-directed cam pins within its inner cavity that ride within the undulating groove 70. As will be explained, axial movement of the male cam member 64 over the female cam member 68 causes rotation of the latter from camming engagement between the cam pins and the groove 70.

An internally-threaded nut 72 has a plurality of axial through holes (not numbered) that receive prongs 74 extending from the distal end of the female cam member 68. In this way, the nut 72 rotates with the female cam member 68. It should be understood that prongs in through holes is just one way to rotatably couple the two components 68, 72, and other means such as keys, threading, adhesive, a weld, etc. may be used. The nut 72 threadingly engages an elongated threaded shaft 76 attached to the distal end cap 52*b*. The nut 72 also axially abuts a proximal end of an enlarged push member 78 which in turn is in contact with the distal end cap 52*b*. As will be described, advancement of the nut 72 on the shaft 76 displaces the push member 78 which in turn pushes on the distal end cap 52*b*.

With reference to FIG. 4B, the internal tensioning mechanism is shown assembled without the auxetic shape memory alloy stent 50 just prior to actuation. FIG. 4C shows a step after a user pushes the actuation rods 62 while holding fixed the proximal end cap 52*a* (indicated by a proximal arrow). The reader will keep in mind that, during this process, the proximal and distal end caps 52*a*, 52*b* are connected by the outer stent 50 (not shown). The actuation rods 62 distally displace the male cam member 64 which causes rotation of the female cam member 68 as shown. This, in turn, rotates the nut 72 which rides distally along the threaded shaft 76 and displaces the push member 78. It should be understood here that the axial force applied to the male cam member 64 is multiplied via the mechanical advantage of the nut 72 and shaft 76 interface.

In any event, the push member 78 is in contact with the distal end cap 52*b* and the distal force applied thereto is transmitted to the connected outer stent 50, which is held by the proximal end cap 52*a*. This creates tension in the stent 50 and actuates its auxetic shape change, such as seen between FIGS. 2A and 2B. Stated another way, tension applied to the stent 50 causes its expansion. By virtue of the engagement of the threaded shaft 76 by the nut 72, the axial tension applied to the stent is maintained. That is, any axial reaction force transmitted back from the stent 50 travels ultimately to the nut 72, which remains in its relative axial position on the shaft 76, thus locking the actuated coapting element 30 in its expanded shape.

Kink-Resistant Catheter

Tubing kink resistance is a known, desirable characteristic of catheters. In minimally-invasive applications, as in the present context, catheters are required to track through tortuous pathways. The ability to remain free from kinks is integral to maintaining, for example, catheter pushability, lumen patency, and functional mechanical performance. Kink resistance, traditionally, has been increased by creating thicker walled catheters and/or by adding a braid layer in the catheter walls. To this point, thin-walled catheters without braid reinforcement are generally considered to perform most poorly in regard to kink resistance. The present application contemplates improved kink performance for thin-walled catheters for cases where simple braid reinforcement and/or increased wall thickness does not work or is not an option due to design constraints.

Figures 5, 5A, 5B, 6A, 6B:
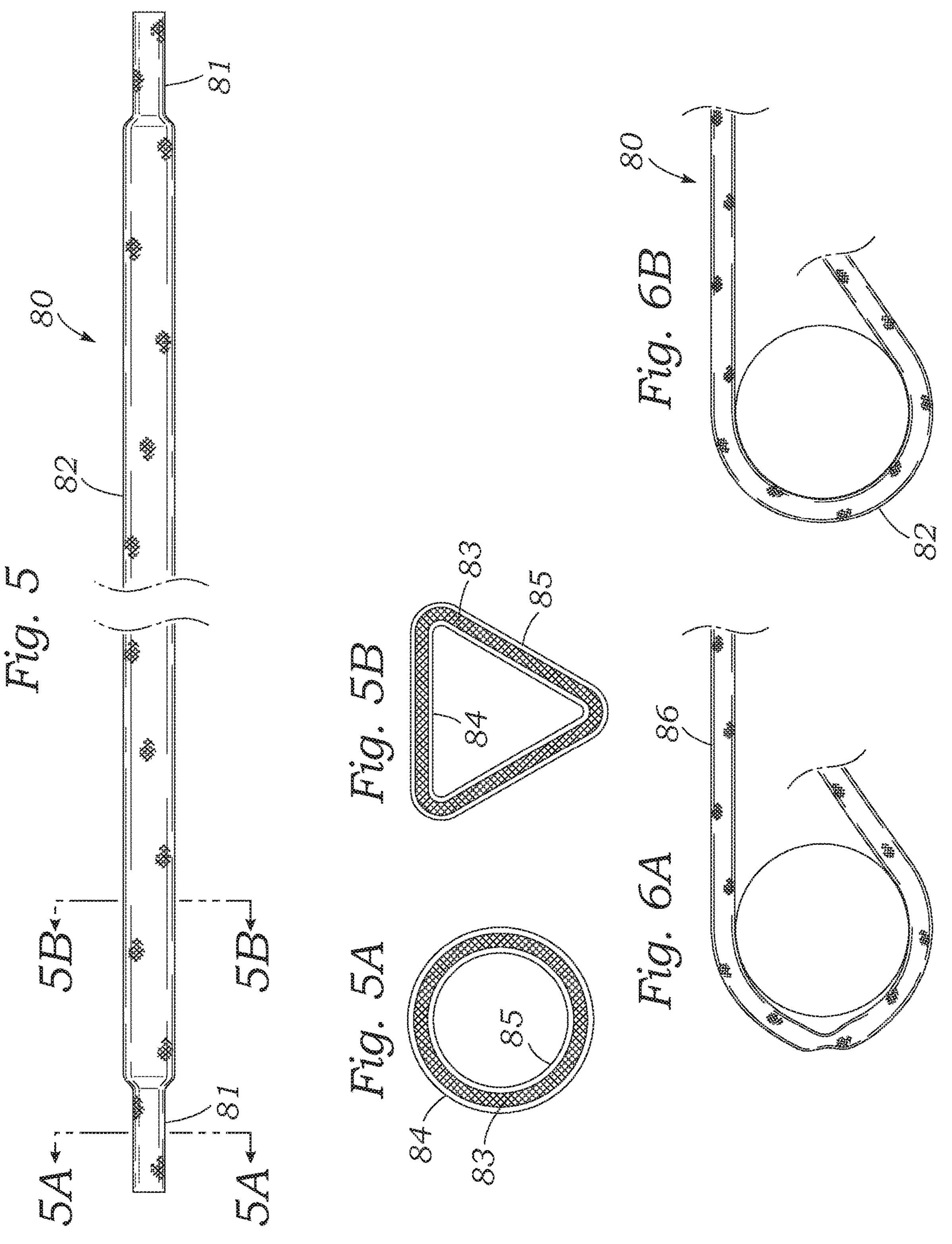
FIG. 5 is an elevational view of an alternative kink-resistant catheter used with the percutaneous heart valve regurgitation reduction system described herein having circular cross-sectional ends as in FIG. 5A and a triangular cross-sectional midportion as seen in FIG. 5B.
FIG. 6A shows a conventional tubular catheter kinked when bent around a cylindrical object.
FIG. 6B shows a catheter with the triangular cross-sectional midportion bent around the same cylinder.

FIG. 5 is an elevational view of an alternative kink-resistant catheter sheath 80 that may be used with the percutaneous heart valve regurgitation reduction system described herein. The catheter sheath 80 preferably has circular cross-sectional ends 81, as shown in FIG. 5A, and a triangular cross-sectional midportion 82, as shown in FIG. 5B. The catheter sheath 80, as with the earlier-described catheter 24, preferably includes a braided central tube 83 bracketed on the inside and outside by an inner polymer layer 84 and an outer polymer layer 85. An initial tubular blank of the catheter sheath 80 may be formed by a co-extrusion of the two polymer layers 84, 85 around the braided central tube 83. The triangular midportion 82 may then be formed by pressure optionally supplemented by heat, such as by tightening a three-pronged drill chuck or similar expedient around the tubular blank with no inner support. In one preferred embodiment, the initial tubular catheter is a braided catheter assembly having an ID of about 1.9 mm and an OD of about 2.4 mm. The two polymer layers 84, 85 are desirably formed of Carbothane, with the braided central tube 83 being an austenitic stainless steel such as 316LVM available from Fort Wayne Metals of Fort Wayne, Ind.

Altering a catheter lumen to enhance performance is known. For instance, U.S. Pat. No. 8,721,588 to Echarri, et al. suggests modifying the inner lumen of a catheter to improve kink performance as well as torque-ability.

In contrast, the kink-resistant catheter sheath 80 described herein is expected to have better kink performance than the Echarri, et al. catheters as the modified cross-section extends to the outer diameter of the catheter. This creates a linear bending moment throughout the entire wall. The triangular cross-sectional shape provides better kink performance when the catheter is bent along any of the three triangular faces tangent to the bending moment. In addition, this disclosure identifies a way of mechanically working a catheter post-reflow (i.e., after the initial polymer extrusion and cooling) to induce linear bending moments. Post-working a catheter after reflow could be advantageous because it would allow thin-walled catheters to be created with flat faces.

To demonstrate the kink behavior of different cross-sections, tests were performed on both traditional tubular and the present triangular cross-section catheter sheath 80. FIG. 6A shows a conventional tubular catheter 86 when bent around a particular diameter cylindrical object, and FIG. 6B shows the catheter sheath 80 with the triangular cross-sectional midportion 82 bent around the same size cylinder. The catheter sheath 80 was formed using the same diameter tubular blank as the tubular catheter 86 (i.e., ID 1.91 mm, OD 2.41 mm). In the tests shown in FIGS. 6A and 6B, the pin diameter was 1.14 cm (0.449"). The tubular catheter kinks before the triangular cross-section catheter sheath 80, and thus any system disclosed herein may include the alternative catheter sheath 80. Moreover, the limit of the kink-resistance for the two catheters 80, 86 was explored. In a test involving 10 samples of the same size catheters, the wholly tubular catheter 86 kinked at an average of about 1.14 cm (0.449"), while the alternative catheter sheath 80 with the triangular cross-sectional midportion 82 kinked at an average pin diameter of 0.43 cm (0.168"), a reduction in potential bend diameter to less than 40% of the conventional tube design. A similar reduction in bend diameter and thus improvement in kink-resistance is expected with different-sized catheters, and thus a thinner-walled catheter may be utilized.

Anti-Tetrachiral Auxetic Stents

Figure 7A:
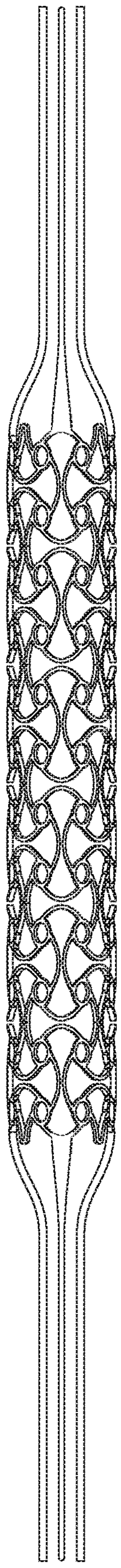
FIG. 7A is an elevational view of an auxetic structure that may be used in an alternative coapting element of the present application.
Figure 7B:
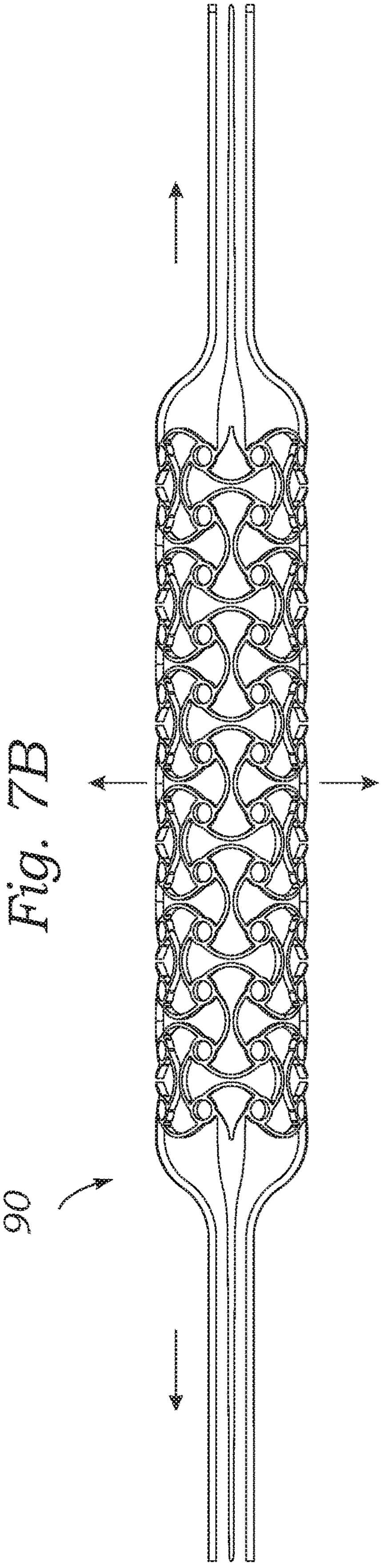
FIG. 7B shows radial expansion thereof.

FIG. 7A is an elevational view of an auxetic structure 90 that may be used in an alternative coapting element of the present application, and FIG. 7B shows radial expansion thereof.

Figure 8B:
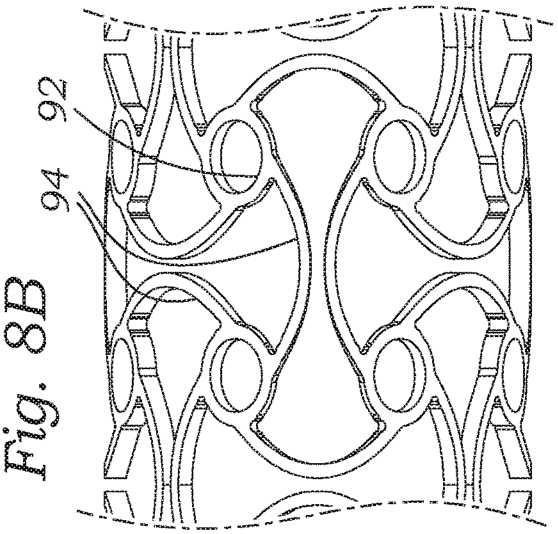
FIGS. 8A and 8B are enlarged views of an auxetic structure used in the coapting element of FIGS. 7A and 7B.
Figure 8A:
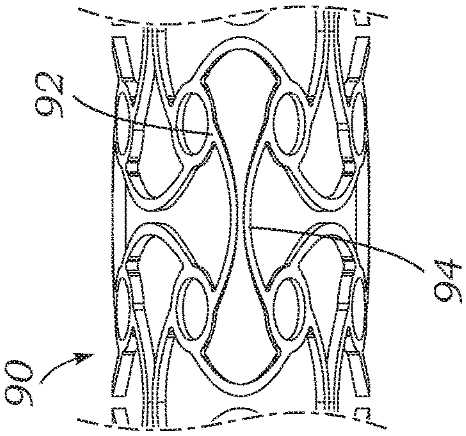

FIGS. 8A and 8B are enlarged views of the exemplary auxetic structure 90 used in the coapting element of FIGS. 7A and 7B. The exemplary laser-cut anti-tetrachiral pattern includes a plurality of evenly-spaced circular rings or hubs 92 connected to other adjacent hubs by arcuate struts 94. In the illustrated embodiment, the pattern features sets of four adjacent circular hubs 92 forming a square or rectangle around the tubular structure 90 each connected by four arcuate struts 94. Pulling on the ends of the expandable structure 90 tends to straighten the arcuate struts 94 which generally aligned with the longitudinal axis of the device. Movement arrows are shown on two of these longitudinally-oriented struts 94 which tend to move away from one another. At the same time, this movement tends to rotate the connected circular hubs 92, as shown by the rotational movement arrows. Both the spreading a part of the longitudinally-oriented struts 94 and the rotation of the circular hubs 92 tends to straighten out the circumferentially-oriented struts 94, as shown. Of course, other patterns may be utilized to result in an auxetic structure having a negative Poisson's ratio.

Figure 9B:
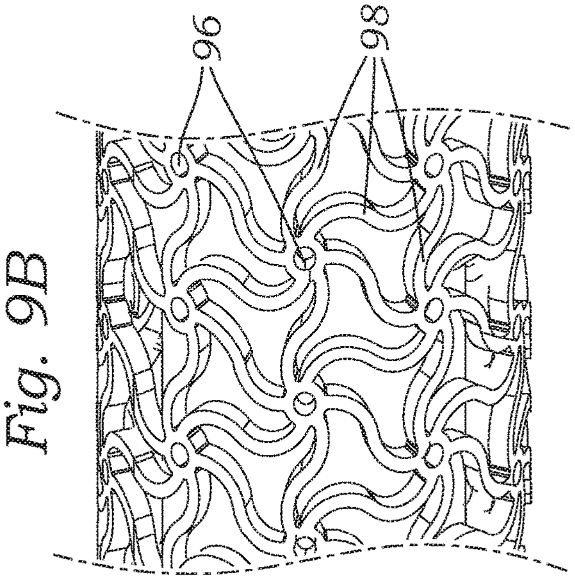
FIGS. 9A and 9B are enlarged views of an auxetic structure used in the coapting element of FIGS. 2A and 2B.
Figure 9A:
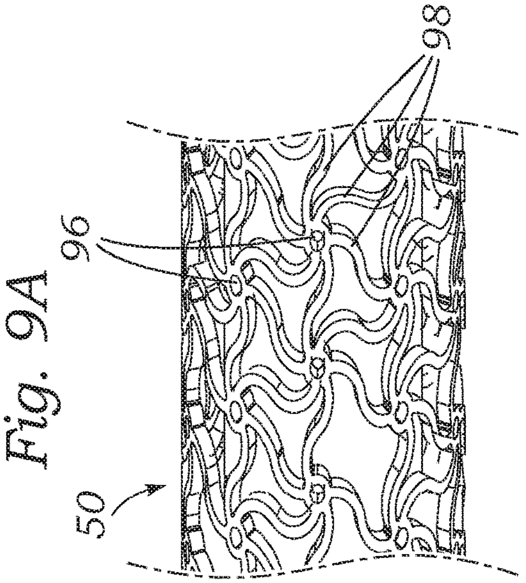

For example, another laser-cut anti-tetrachiral pattern is seen in the stent 50 of FIGS. 2A and 2B, enlarged in FIGS. 9A and 9B. In this pattern, a plurality of hubs 96 in the form of circular rings are evenly distributed around the stent 50 in both the longitudinal and circumferential directions. Each adjacent pair of hubs 96 is connected by one of a plurality of serpentine struts 98. In the preferred embodiment, the hubs 96 are distributed in a hexagonal pattern with each hub that is not on a longitudinal end of the stent 50 being surrounded by six identical and identically-spaced hubs at 60° intervals. As seen by the transition between FIGS. 9A and 9B, longitudinal tension on the stent 50 straightens the serpentine struts 98 and radially expands the stent.

Auxetic Foam

Figure 10B:
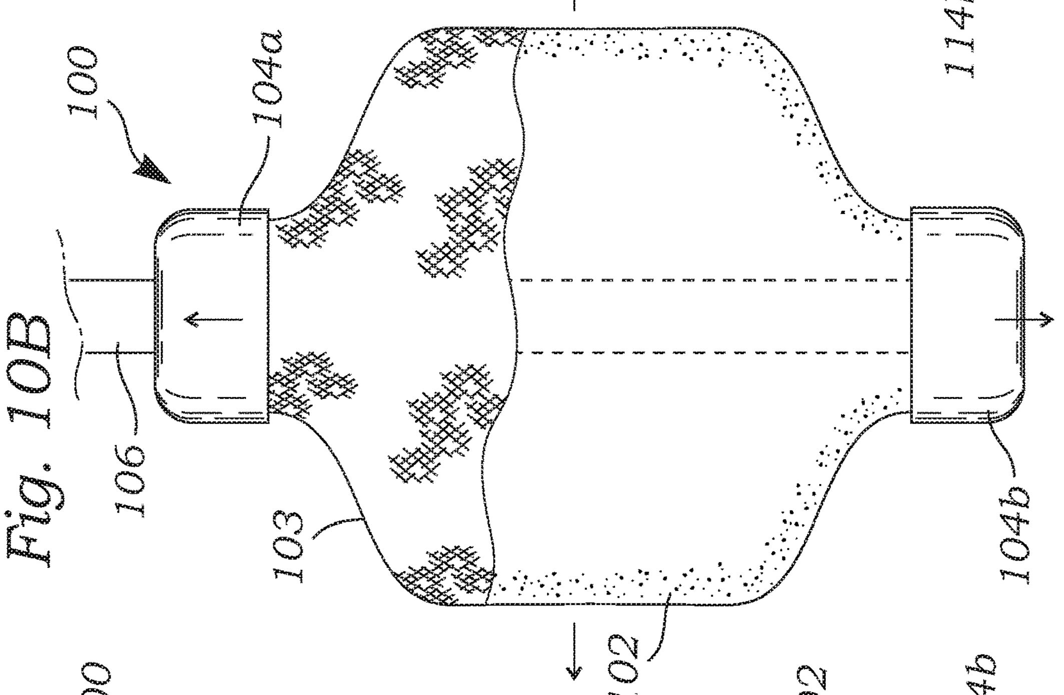
FIGS. 10A and 10B are side views of another adjustable coapting element having an auxetic foam structure.
Figure 10A:
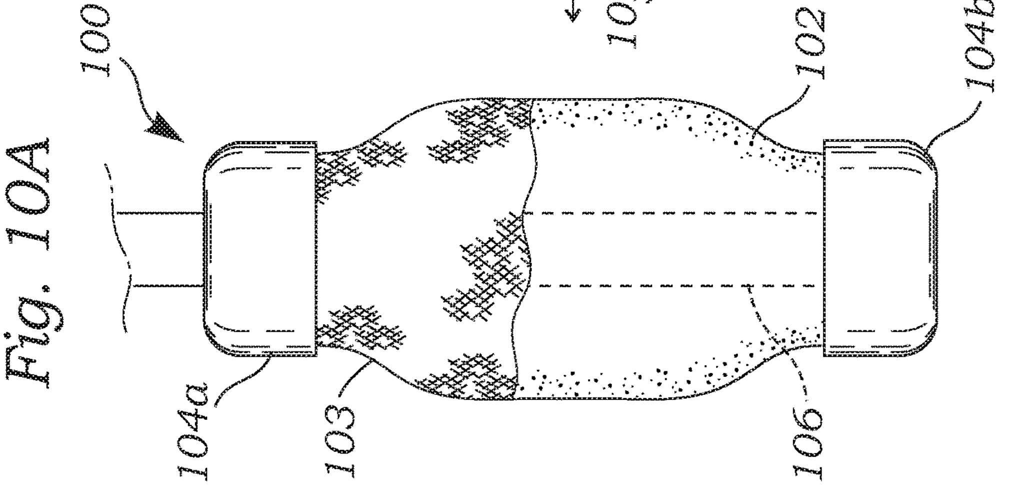

FIGS. 10A and 10B are side views of another adjustable coapting element having an auxetic foam structure. Lakes, R. S., et al. (Foam Structures with a Negative Poisson's Ratio," Nature, 253:1038, 1987) disclosed that conventional polyurethane foams can undergo processing to alter cell structure and converts the foam from having a positive Poisson's ratio to a negative Poisson's ratio. Smith, et al. (A Novel Mechanism for Generating Auxetic Behaviour in Reticulated Foams: Missing Rib Foam Model, Acta mater. 48 (2000) 4349-4356, 2000) disclosed a method for creating this foam.

However, these foams have not been investigated for applicability in medical devices. The present application proposes to cut a conventional polyurethane foam to a desired implant geometry and heat/pressure-treat the foam in accordance with Smith, et al. to obtain a negative Poisson's ratio. Such a foam element can then be axially strained to swell the diameter and axially compressed to reduce the implant diameter. This implant is appealing because it builds on the existing spacer platforms and adds continuous up-sizing or down-sizing.

In one form, FIGS. 10A and 10B illustrate a coapting element 100 including a central auxetic foam member 102 preferably having an outer hyper-elastic cover 103 and coupled at both ends to proximal and distal end caps 104*a*, 104*b*. The cover 103 helps reduce detrimental friction/abrasion between the foam member 102 and the surrounding valve leaflets. The coapting element 100 is located at a distal end of a catheter 106 which includes a mechanism (not shown) for applying longitudinal strain to the end caps 104*a*, 104*b*. FIG. 10A shows the coapting element 100 in a reduced diameter state as would be seen during delivery to a target implant site, while FIG. 10B shows the end caps 104*a*, 104*b* pulled apart to apply strain to the auxetic foam member 102, causing it to radially expand. As with the auxetic stent 50 described above, the ability to adjust the radial size of the auxetic foam member 102 permits continuous up-sizing or down-sizing of the coapting element 100 in vivo, and real time adjustment of the performance of the coapting element 100 under fluoroscopy or other form of visualization.

Figure 11:
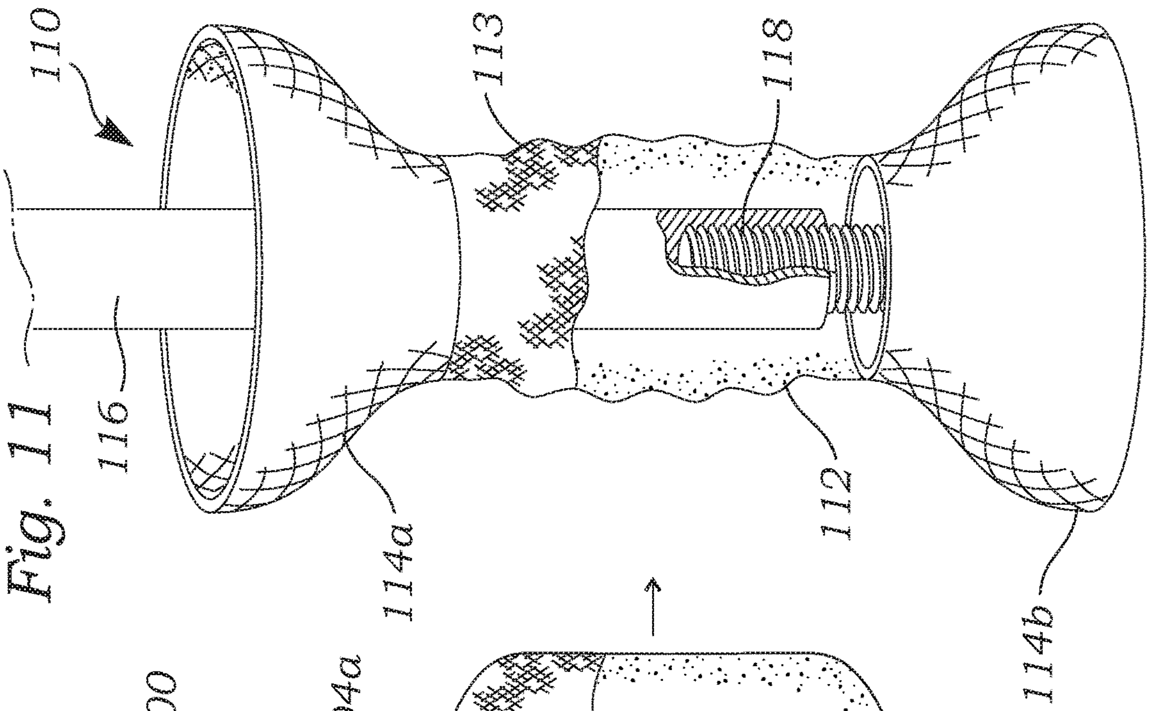
FIG. 11 is a perspective view of a still further adjustable coapting element having an auxetic foam central structure and self-expanding end stents.

FIG. 11 is a perspective view of a still further adjustable coapting element 110 having an auxetic foam central structure 112 preferably having an outer hyper-elastic cover 113 and self-expanding end stents 114*a*, 114*b*. Again, the cover 113 helps reduce detrimental friction/abrasion between the auxetic foam structure 112 and the surrounding valve leaflets. As with the auxetic foam member 102 of FIGS. 10A/10B, the auxetic foam central structure 112 expands radially when subjected to axial tension/strain. One embodiment for lengthening the central structure 112 is a telescoped arrangement of a female end of a delivery catheter 116 that engages a male threaded shaft 118 secured to the distal end stent 114*b*. More particularly, the central structure 112 is secured to the end stents 114*a*, 114*b* and the catheter 116 is fixed with respect to the proximal end stent 114*a*. By rotating the catheter 116 the distance between the end stents 114*a*, 114*b* may be adjusted to simultaneously adjust the radial size of the auxetic foam central structure 112 until a desired regurgitant grade reduction is achieved.

Mechanical Expanders

FIG. 12 is a side view of an adjustable coapting element 120 having a number of coiled strips 122 which alter a shape of the element. More particularly, double-sided, constant-force spring strips 122 are concentrically spaced (such as three as shown) and coiled at ends 123 around two end rings 124. The user may increase or decrease the distance between the rings 124 to increase or decrease the diameter of the coapting element 120. Specifically, as seen by the transition between FIGS. 13A and 13B, each coil strip 122 experiences a reduction in diameter of the end coils when the end rings 124 are spaced farther apart. The distance between the end rings 124 may be adjusted via a telescoped smaller tube 126 within a larger catheter tube 128. The tubes 126, 128 are respectively coupled to the end rings 124 via spokes 130. Linear displacement of the inner tube 126 relative to the outer tube 128 changes the distance between the rings 124. The number of coil strips 122 may be varied, but is desirably between three and eight. The exterior of the coil strips 122 themselves may be formed of a suitable material to contact the heart valve leaflets and reduce regurgitation. For instance, the coil strips 122 may have a cover of suitable polymer (e.g., Carbothane) or even bioprosthetic tissue over a resilient material that forms the springs. Alternatively, the entire structure maybe surrounded by a hyper-compliant open or closed cover 132 (shown in phantom) that is expandable and comes in direct contact with the leaflets.

Figure 14:
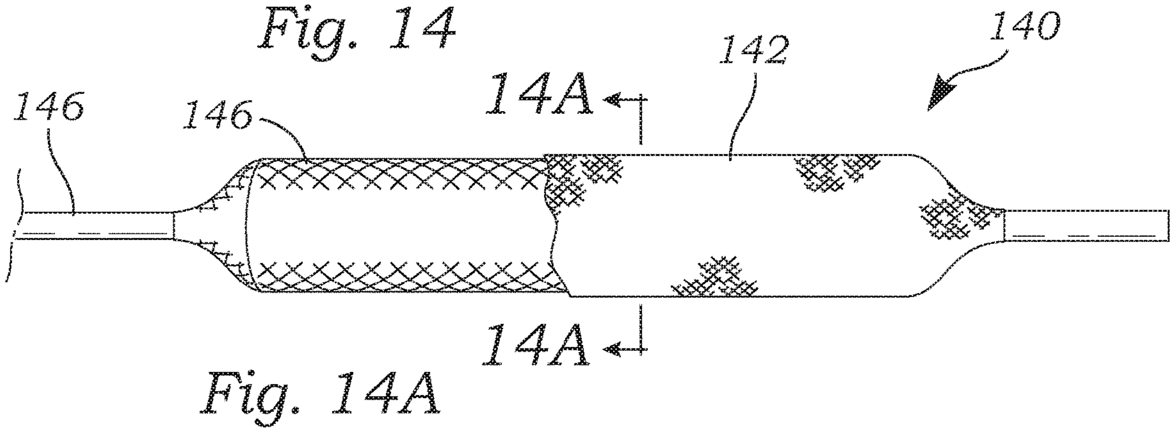
FIG. 14 is a side view of an adjustable coapting element that uses an inflatable sandwiched structure.
Figure 14A:
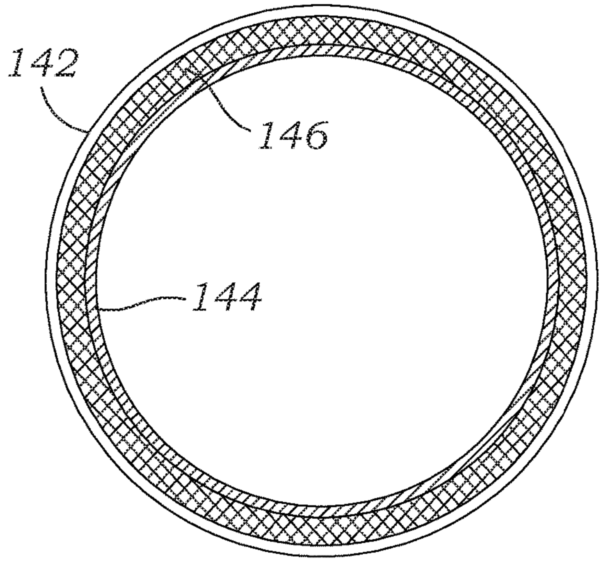
FIG. 14A is a sectional view therethrough.

FIG. 14 is a side view of an adjustable coapting element 140 that uses an inflatable sandwiched structure, and FIG. 14A is a sectional view therethrough. The coapting element 140 includes an outer cover 142, an inner balloon 144, and an intermediate stent 146 sandwiched there between. The coapting element 140 connects at both ends to a delivery catheter 148 which includes an inflation lumen (not shown) for increasing or decreasing the pressure within the inner balloon 144. The stent 146 consists of a positive Poisson's ratio stent which undergoes a proportional shortening in length when radially expanded. The coapting element 140 is closed (with a tight seal to a railing shaft as described in U.S. Pat. No. 9,474,605) at the distal end and open to inflation/deflation such as by using a manual syringe-type device made by Atrion Medical of Arab, Ala. The coapting element 140 is crimped and delivered to the desired anatomical location. Once at the location, the coapting element 140 is inflated to the desired size. The coapting element 140 can be further up-sized by adding more pressure to the system or down-sized by holding back-pressure.

Figure 15A:
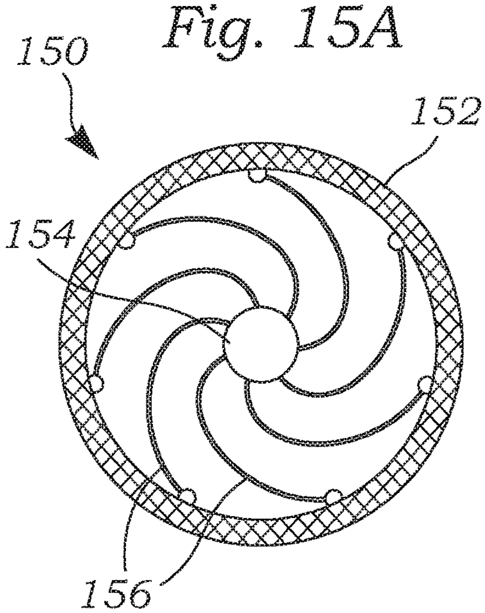
FIGS. 15A and 15B are sectional views through an adjustable coapting element with an outer cover connected to and shaped by a rotating core and spiral spokes.
Figure 15B:
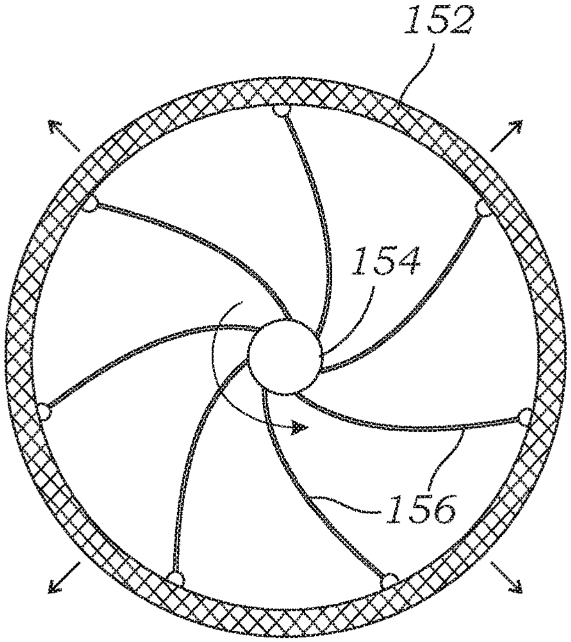

FIGS. 15A and 15B are sectional views through a still further adjustable coapting element 150 with an outer cover 152 connected to and shaped by a rotating core 154 via spirally-dispersed, curved cantilever spokes 156. The outer cover 152 may be a hyper-compliant polymeric (e.g., Carbothane) or tissue material that is capable of significant radial expansion. The outer cover 152 preferably also incorporates a positive Poisson's ratio stent. Rotating the inner core 154 while holding the outer cover 152 stationary straightens the spiral spokes 156 and thus expands the coapting element 150. Similar to versions described above, the coapting element 150 maybe mounted to a distal end of a delivery catheter (not shown) to which the cover 152 attaches, with the inner core 154 passing through a lumen in the catheter. In an exemplary configuration, the spokes 156 are made of a Nitinol or similar hyperelastic alloy. The shape (circular, rectangular, etc.) to which the outer cover 152 deploys can be modulated by reducing or increasing the number of beams. More beams equate to a more circular deployed structure. In an example configuration, a triangle deployed shape might be constructed by fabricating a coapting element 150 with three attachment points. The diameter range of the deployed stent can be tightly controlled by the length of the spokes 156. Longer spokes 156 may translate into a bigger range of deployable diameters. In one embodiment, the outer cover 152 incorporates a plastically-expandable stent that retains its expanded shape such that the expansion mechanism may be removed by releasing the attachment points of the spokes 156 to the stent once a desired size is reached.

Figure 16A:
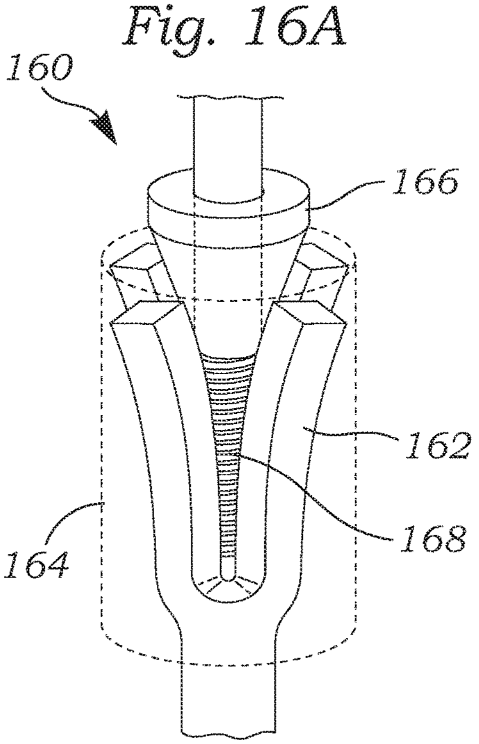
FIGS. 16A and 16B are side views of an adjustable coapting element with a plurality of deflectable fingers that reshape an outer cover.
Figure 16B:
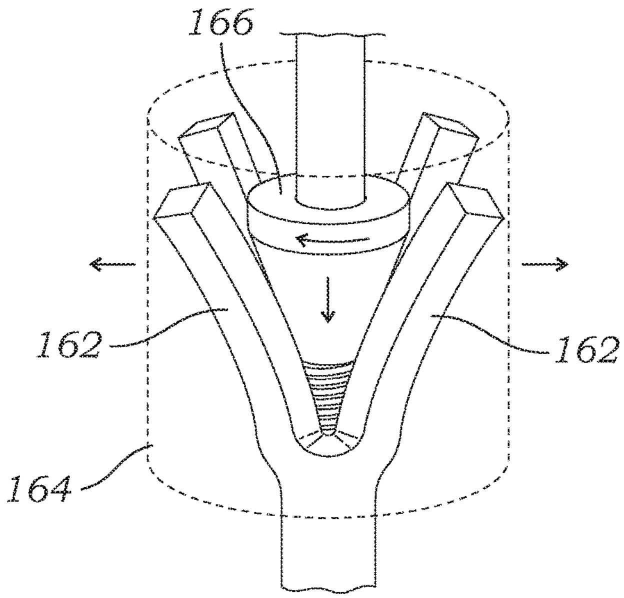

FIGS. 16A and 16B are side views of another adjustable coapting element 160 with a plurality of deflectable fingers 162 that reshape an outer cover 164. A tapered driver 166 acts against inner surfaces of the deflectable fingers 162 which are in turn attached to the outer cover 164. By advancing the driver 166 along a threaded rod 168 the driver cams apart the deflectable fingers 162 and increases the diameter of the coapting element 160, and vice versa. In an alternative configuration, the coapting element 160 consists of two polymer pieces. A first piece 162, which contacts the leaflet surfaces, is a soft, pronged piece with a tapered, threaded inner diameter. The second piece is a tapered drive screw 166 that may be translated distally within the first piece 162, thus separating the polymer prongs to increase the diameter of the implant. Likewise, the diameter can be reduced by retracting the drive screw 166. As before, the outer cover 164 may be a hyper-compliant polymeric or tissue material capable of significant radial expansion, and may also incorporate a positive Poisson's ratio stent.

Figure 17:
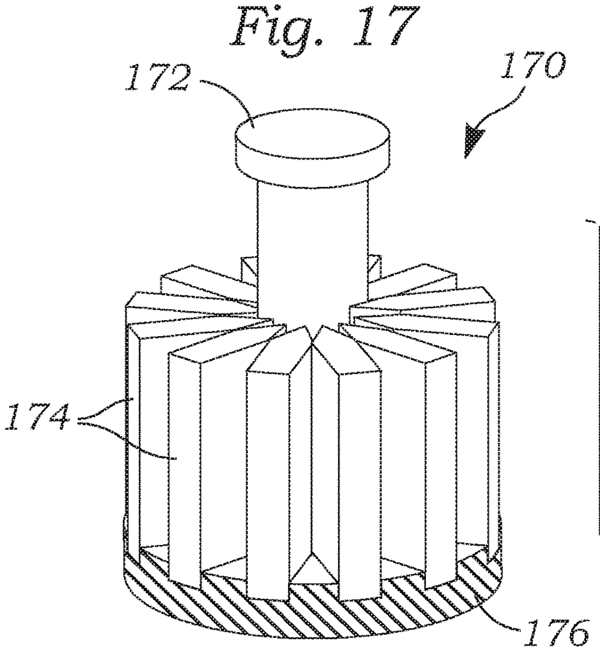
FIG. 17 is a perspective view of an inner portion of an adjustable coapting element that uses a cam pin to displace a number of wedge-shaped members radially outward.
Figure 17A:
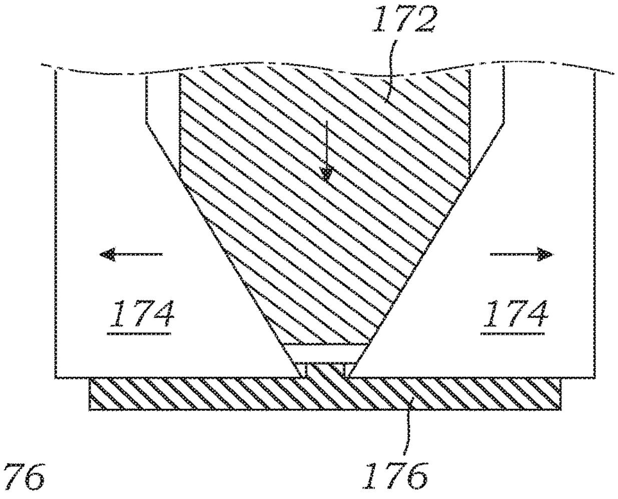
FIG. 17A is a radial section showing the camming action.

FIG. 17 is a perspective view of an inner portion of an adjustable coapting element 170 that uses a tapered cam pin 172 to displace a number of wedge-shaped members 174 radially outward. FIG. 17A is a radial section showing the camming action. The wedge-shaped members 174 may be guided in channels formed in a base member 176. The tapered cam pin 172 engages the tapered wedge-shaped members 174 that move radially outward as the cam pin 172 advances. Although not shown, a stent could surround and be attached to the outer surfaces of the members 174. The stent would expand as the tapered cam pin 172 moves downward. The members 174 could also be attached to a spring mechanism that urges recoil of the outward members 174 and stent as the tapered cam pin 172 retracts. This action would allow down-sizing of the coapting element 170. In one embodiment, the outer cover stent is plastically-expandable and retains its expanded shape such that the expansion mechanism may be removed by inwardly constricting the wedge-shaped members 174 out of contact with the stent once a desired size is reached.

Inflatable Actuator

Figures 18, 18A:
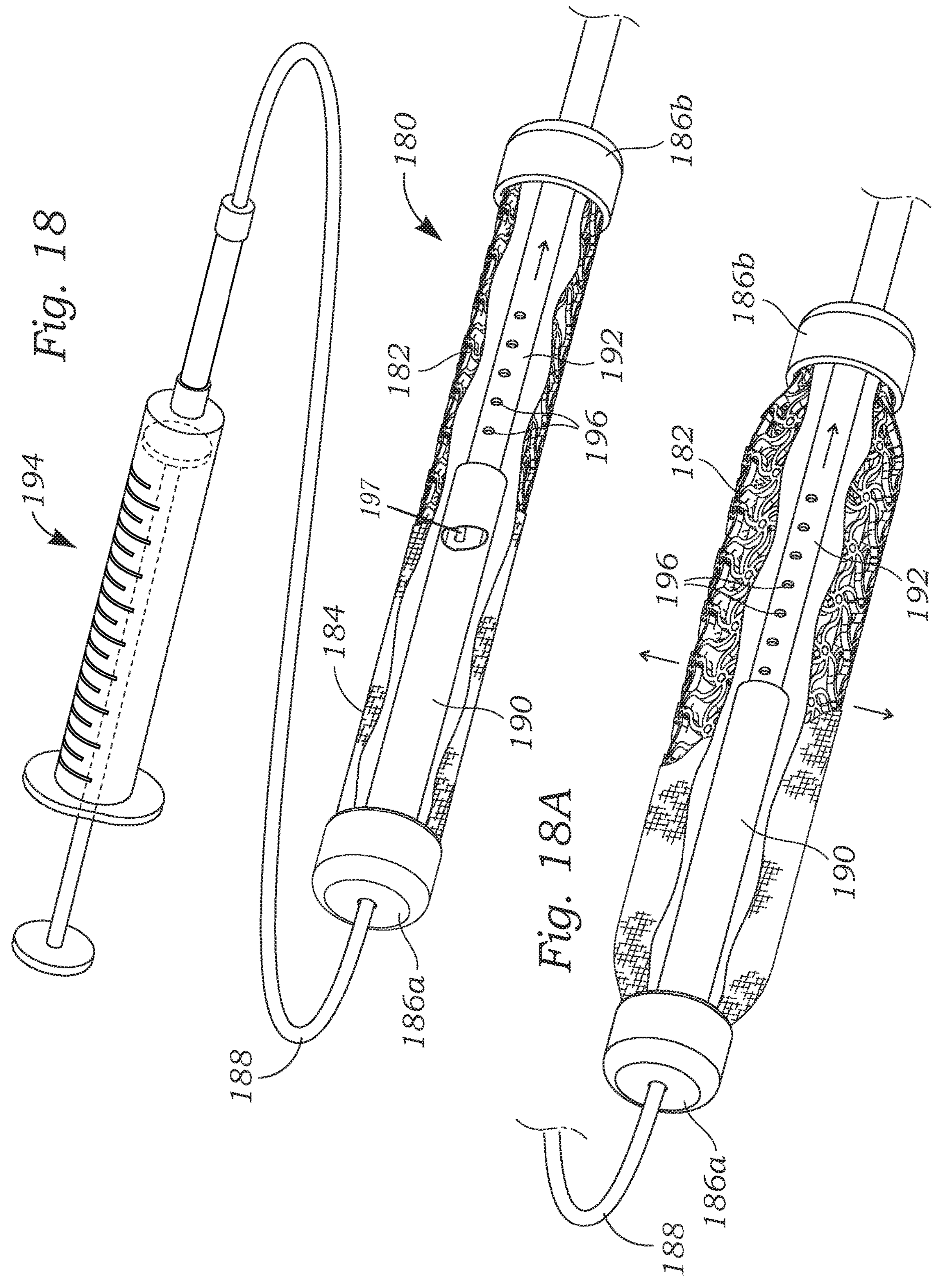
FIG. 18 is a perspective view of a system that uses fluid pressure to reshape an adjustable coapting element shown partly cutaway.
FIG. 18A shows the coapting element in an expanded state.

FIG. 18 is a perspective view of a system that uses fluid pressure to reshape an adjustable coapting element 180 shown partly cutaway, and FIG. 18A shows the coapting element in an expanded state. The coapting element 180 is similar to the element 30 described above with reference to FIGS. 2-4 but with a different linear expansion configuration. More particularly, the coapting element 180 includes an inner laser-cut, pre-compressed anti-tetrachiral auxetic stent 182 surrounded by an outer cover 184. As before, the auxetic stent 182 is connected at both ends to end caps 186*a*, 186*b*. An elongated flexible catheter 188 extends through a proximal end cap 186*a* to an internal chamber of a cylinder 190 that is fixedly connected to the proximal end cap. In a preferred embodiment, the flexible catheter 188 is smaller and passes through the aforementioned larger catheter sheath 24. A piston 192 telescopically slides within the cylinder 190 and is connected to the distal end cap 186*b*. A source of inflation fluid, such as the syringe 194 shown, may be used to adjust the pressure within the cylinder 190 so as to extend or retract the piston 192. Index holes 196 may be provided in the piston 192 that register with a pawl (shown at 197 in cutaway) extending inward from the cylinder 190 so as to lock the extended length of the assembly in place. By applying strain to the end caps 186 in this way, the auxetic stent 182 radially expands.

While the foregoing is a complete description of the preferred embodiments of the invention, various alternatives, modifications, and equivalents may be used. Moreover, it will be obvious that certain other modifications may be practiced within the scope of the appended claims.

What is claimed is:

1. An elongated percutaneously-implanted system for reducing regurgitation through a native heart valve, comprising:

an elongated catheter sheath having a length sufficient to extend from outside the body to a native heart valve via the subclavian vein and superior vena cava;

an expandable coapting element mounted to a distal end of the catheter sheath, the expandable coapting element having an auxetic structure surrounded by an outer cover, the auxetic structure being a metallic stent having an anti-tetrachiral strut pattern configured to exhibit a negative Poisson's ratio and the metallic stent being connected to opposite longitudinal end caps, the expandable coapting element being collapsible and expandable to a diameter sufficient to plug a regurgitant hole between valve leaflets in order to reduce regurgitation through the native heart valve; and a tensioning mechanism controlled from a proximal end of the catheter sheath and extending through the expandable coapting element, the tensioning mechanism being between and in contact with the opposite longitudinal end caps, and the tensioning mechanism being configured to apply tension capable of pulling one of the opposite longitudinal end caps away from the other and thus elongate and radially expand the auxetic structure, and the tensioning mechanism comprises a piston-cylinder assembly that extends through the metallic stent between the opposite longitudinal end caps and is supplied with an inflation fluid through a flexible secondary catheter that passes through the catheter sheath.

2. The system of claim 1, wherein the outer cover is a hyper-compliant polymer.

3. The system of claim 1, wherein the catheter sheath has a kink-resistant mid-portion that has a triangular cross-sectional shape.

4. The system of claim 1, wherein the metallic stent is tubular and the anti-tetrachiral strut pattern includes a plurality of evenly-spaced circular hubs that are ring-shaped each connected to adjacent hubs of the circular hubs by arcuate struts.

5. The system of claim 4, wherein the anti-tetrachiral strut pattern has sets of four hubs of the circular hubs, each hub in each set being adjacent to the other hubs in the set and the sets each forming a square or rectangle around the tubular metallic stent, each set of four hubs connected by four arcuate struts.

6. The system of claim 1, wherein the metallic stent is tubular and the anti-tetrachiral strut pattern includes a plurality of circular hubs that are ring-shaped and evenly distributed around the tubular metallic stent in both longitudinal and circumferential directions, and adjacent pairs of the circular hubs are connected by one of a plurality of serpentine struts.

7. The system of claim 6, wherein the circular hubs are distributed in a hexagonal pattern with each circular hub that is not on a longitudinal end of the tubular metallic stent being surrounded by six identical and identically-spaced hubs of the circular hubs at 60° intervals.

8. The system of claim 1, wherein the flexible secondary catheter extends through a proximal one of the opposite longitudinal end caps to an internal chamber of a cylinder of the piston-cylinder assembly.

9. The system of claim 8, wherein index holes are provided in a piston of the piston-cylinder assembly that register with a pawl extending inward from the cylinder so as to lock an extended length of the piston-cylinder assembly in place.

10. An elongated percutaneously-implanted system for reducing regurgitation through a native heart valve, comprising:

an elongated catheter sheath having a length sufficient to extend from outside the body to a native heart valve via the subclavian vein and superior vena cava;

an expandable coapting element mounted to a distal end of the catheter sheath, the expandable coapting element having an auxetic structure surrounded by an outer cover, the auxetic structure being a metallic stent having an anti-tetrachiral strut pattern configured to exhibit a negative Poisson's ratio and the metallic stent being connected to opposite longitudinal end caps, the expandable coapting element being collapsible and expandable to a diameter sufficient to plug a regurgitant hole between valve leaflets in order to reduce regurgitation through the native heart valve, wherein the metallic stent is tubular and the anti-tetrachiral strut pattern includes a plurality of evenly-spaced circular hubs that are ring-shaped each connected to adjacent hubs of the circular hubs by arcuate struts; and a tensioning mechanism controlled from a proximal end of the catheter sheath and extending through the expandable coapting element, the tensioning mechanism being between and in contact with the opposite longitudinal end caps, and the tensioning mechanism being configured to apply tension capable of pulling one of the opposite longitudinal end caps away from the other and thus elongate and radially expand the auxetic structure.

11. The system of claim 10, wherein the anti-tetrachiral strut pattern has sets of four hubs of the circular hubs, each hub in each set being adjacent to the other hubs in the set and the sets each forming a square or rectangle around the tubular metallic stent, each set of four hubs connected by four arcuate struts.

12. The system of claim 10, wherein the tensioning mechanism extends through the metallic stent between the opposite longitudinal end caps and includes a plurality of flexible actuation rods that pass through the catheter sheath and through a proximal end cap, the actuation rods acting on a first cam member to rotate a second cam member and advance a nut over a threaded rod, the nut causing a distal end cap of the opposite longitudinal end caps to be displaced distally with respect to the proximal end cap.

13. The system of claim 10, wherein the tensioning mechanism comprises a piston-cylinder assembly that extends through the metallic stent between the opposite longitudinal end caps and is supplied with an inflation fluid through a flexible secondary catheter that passes through the catheter sheath, and wherein the flexible secondary catheter extends through a proximal one of the opposite longitudinal end caps to an internal chamber of a cylinder of the piston-cylinder assembly.

14. The system of claim 13, wherein index holes are provided in a piston of the piston-cylinder assembly that register with a pawl extending inward from the cylinder so as to lock an extended length of the piston-cylinder assembly in place.

15. The system of claim 10, wherein the outer cover is a hyper-compliant polymer.

16. The system of claim 10, wherein the catheter sheath has a kink-resistant mid-portion that has a triangular cross-sectional shape.

17. An elongated percutaneously-implanted system for reducing regurgitation through a native heart valve, comprising:

an elongated catheter sheath having a length sufficient to extend from outside the body to a native heart valve via the subclavian vein and superior vena cava;

an expandable coapting element mounted to a distal end of the catheter sheath, the expandable coapting element having an auxetic structure surrounded by an outer cover, the auxetic structure being a metallic stent having an anti-tetrachiral strut pattern configured to exhibit a negative Poisson's ratio and the metallic stent being connected to opposite longitudinal end caps, the expandable coapting element being collapsible and expandable to a diameter sufficient to plug a regurgitant hole between valve leaflets in order to reduce regurgitation through the native heart valve, wherein the metallic stent is tubular and the anti-tetrachiral strut pattern includes a plurality of circular hubs that are ring-shaped and evenly distributed around the tubular metallic stent in both longitudinal and circumferential directions, and adjacent pairs of the circular hubs are connected by one of a plurality of serpentine struts; and a tensioning mechanism controlled from a proximal end of the catheter sheath and extending through the expandable coapting element, the tensioning mechanism being between and in contact with the opposite longitudinal end caps, and the tensioning mechanism being configured to apply tension capable of pulling one of the opposite longitudinal end caps away from the other and thus elongate and radially expand the auxetic structure.

18. The system of claim 17, wherein the circular hubs are distributed in a hexagonal pattern with each circular hub that is not on a longitudinal end of the tubular metallic stent being surrounded by six identical and identically-spaced hubs of the circular hubs at 60° intervals.

19. The system of claim 17, wherein the tensioning mechanism extends through the metallic stent between the opposite longitudinal end caps and includes a plurality of flexible actuation rods that pass through the catheter sheath and through a proximal end cap of the opposite longitudinal end caps, the actuation rods acting on a first cam member to rotate a second cam member and advance a nut over a threaded rod, the nut causing a distal end cap of the opposite longitudinal end caps to be displaced distally with respect to the proximal end cap.

20. The system of claim 17, wherein the tensioning mechanism comprises a piston-cylinder assembly that extends through the metallic stent between the opposite longitudinal end caps and is supplied with an inflation fluid through a flexible secondary catheter that passes through the catheter sheath, and wherein the flexible secondary catheter extends through a proximal one of the opposite longitudinal end caps to an internal chamber of a cylinder of the piston-cylinder assembly.

21. The system of claim 20, wherein index holes are provided in a piston of the piston-cylinder assembly that register with a pawl extending inward from the cylinder so as to lock an extended length of the piston-cylinder assembly in place.

22. The system of claim 17, wherein the outer cover is a hyper-compliant polymer.

23. The system of claim 17, wherein the catheter sheath has a kink-resistant mid-portion that has a triangular cross-sectional shape.

* * * * *